US012589202B2

(12) United States Patent
Bin et al.

(10) Patent No.: US 12,589,202 B2
(45) Date of Patent: Mar. 31, 2026

(54) LIQUID MEDICINE INJECTION DEVICE

(71) Applicant: EOFLOW CO., LTD., Seongnam-si (KR)

(72) Inventors: Inwook Bin, Yongin-si (KR); Sangjin Han, Gunpo-si (KR); Seungha Kim, Goyang-si (KR); Hyunduk Roh, Seoul (KR); Daejong Park, Seoul (KR)

(73) Assignee: EOFLOW CO., LTD., Seongnam-si (KR)

( * ) Notice: Subject to any disclaimer, the term of this patent is extended or adjusted under 35 U.S.C. 154(b) by 0 days.

(21) Appl. No.: 18/646,783

(22) Filed: Apr. 26, 2024

(65) Prior Publication Data

US 2024/0293616 A1      Sep. 5, 2024

Related U.S. Application Data

(63) Continuation of application No. 18/030,271, filed as application No. PCT/KR2021/013469 on Sep. 30, 2021.

(30) Foreign Application Priority Data

Oct. 6, 2020      (KR) ........................ 10-2020-0128452
Oct. 20, 2020      (KR) ........................ 10-2020-0135924

(51) Int. Cl.
  *A61M 5/142*      (2006.01)
  *A61M 5/172*      (2006.01)
(52) U.S. Cl.
  CPC ........ *A61M 5/172* (2013.01); *A61M 5/14248* (2013.01); *A61M 2005/14252* (2013.01); *A61M 2205/18* (2013.01)

(58) Field of Classification Search
  CPC .............. A61M 5/172; A61M 5/14248; A61M 2005/14252; A61M 2005/206; A61M 2205/18
  See application file for complete search history.

(56) References Cited

U.S. PATENT DOCUMENTS 5,266,013 A * 11/1993 Aubert ................ A61M 5/1413
                                                    417/474
8,137,314 B2 * 3/2012 Mounce .............. A61M 5/1413
                                                    604/151

(Continued)

FOREIGN PATENT DOCUMENTS

JP          05154196          6/1993
JP      2006034323 A      2/2006

(Continued)

OTHER PUBLICATIONS

International Search Report dated Jan. 24, 2022, issued in International Patent Application No. PCT/KR2021/013469.

(Continued)

*Primary Examiner* — Laura A Bouchelle
(74) *Attorney, Agent, or Firm* — PnK IP LLC

(57) ABSTRACT

A medical liquid infusion apparatus includes: a first body to which a needle assembly is mounted, a control module installed in the first body, configured to control driving of the needle assembly, and electrically connected to an internal device, and a fracture portion formed to protrude outward from one side of the control module, and fractured by an external force to allow an electrical connection between the control module and the internal device to be disconnected.

13 Claims, 26 Drawing Sheets

(56)         References Cited

U.S. PATENT DOCUMENTS

| | | | |
|---|---|---|---|
| 8,547,239 | B2 | 10/2013 | Peatfield et al. |
| 10,420,883 | B2 | 9/2019 | Diianni et al. |
| 2020/0086044 | A1 | 3/2020 | Streit et al. |
| 2020/0121848 | A1 | 4/2020 | Schmidlin et al. |
| 2020/0158785 | A1 | 5/2020 | Friedli et al. |

FOREIGN PATENT DOCUMENTS

| | | | |
|---|---|---|---|
| JP | 6014868 | B2 | 10/2016 |
| JP | 2019527086 | | 9/2019 |
| JP | 2020096946 | A | 6/2020 |
| KR | 101521742 | B1 | 5/2015 |
| KR | 1020150107743 | A | 9/2015 |
| KR | 1020150126617 | A | 11/2015 |
| KR | 1020170106053 | A | 9/2017 |
| WO | 2019/038751 | | 2/2019 |
| WO | 2020/068623 | | 4/2020 |

OTHER PUBLICATIONS

Non-Final Office Action dated May 9, 2022, issued in Korean Patent Application No. 10-2020-0128452.
Notice of Allowance dated Nov. 24, 2022, issued in Korean Patent Application No. 10-2020-0128452.
Non-Final Office Action dated Oct. 11, 2023, issued in U.S. Appl. No. 18/030,271.
Notice of Allowance dated Jan. 29, 2024, issued in U.S. Appl. No. 18/030,271.

* cited by examiner

LIQUID MEDICINE INJECTION DEVICE

CROSS REFERENCE TO RELATED APPLICATIONS

This application is a Continuation Application of U.S. application Ser. No. 18/030,271, filed on Apr. 5, 2023, which is a National Stage Entry of International Patent Application No. PCT/KR2021/013469, filed on Sep. 30, 2021, which claims priority from and the benefit of Korean Patent Application Nos. 10-2020-0128452, filed on Oct. 6, 2020, and 10-2020-0135924, filed on Oct. 20, 2020, each of which is hereby incorporated by reference for all purposes as if fully set forth herein.

BACKGROUND

Field

The present disclosure relates to a medical liquid infusion apparatus, and more specifically, to a liquid medicine injection device.

Discussion of the Background

Medical liquid infusion apparatuses such as insulin infusing apparatuses are used to infuse medical liquids into the bodies of patients, and are used by professional medical staff such as nurses or doctors but are mostly used by patients themselves or ordinary persons such as caretakers.

In the case of diabetic patients, particularly pediatric diabetic patients, it is necessary to infuse medical liquids such as insulin into a human body at regular intervals. A patch-type medical liquid infusion apparatus that may be used by being attached to a human body for a predetermined period of time has been developed, and such a medical liquid infusion apparatus may be used while being attached as a patch type to the human body such as the abdomen or waist of a patient for a predetermined period of time.

In order to increase the effect of the medical liquid infusion, the medical liquid infusion apparatus needs to be controlled to precisely infuse the medical liquid into the body of a patient, and accordingly, it is important to precisely infuse a small amount of the medical liquid through a small-sized medical liquid infusion apparatus.

The medical liquid infusion apparatus attached to the human body needs to be comfortable to wear, to be convenient to use, to be durable, and to be driven with low power. In particular, since a patient directly attaches the medical liquid infusion apparatus to the skin and uses it, it is important for a user to drive the medical liquid infusion apparatus conveniently and safely.

In addition, such a medical liquid infusion apparatus normally requires an expiration date of more than one year, and needs to be maintained such that battery consumption is minimized until a period of use, so as to operate without a problem within the period of use guaranteed even when used up to a time point in which the expiration date is imminent.

In addition, the medical liquid infusion apparatus attached to the human body needs to be comfortable to wear, to be convenient to use, to be durable, and to be driven with low power. In particular, since a patient directly attaches the medical liquid infusion apparatus to the skin and uses it, it is important for a user to drive the medical liquid infusion apparatus conveniently and safely.

Conventional medical liquid infusion apparatuses have an alarm function capable of notifying a user of a normal operation or a malfunction, but there is a problem that even in the normal operation, the alarm continues due to an error, causing inconvenience to the user.

The above information disclosed in this Background section is only for understanding of the background of the inventive concepts, and, therefore, it may contain information that does not constitute prior art.

SUMMARY

Embodiments of the present disclosure have been made in an effort to resolve the above problems and/or limitations, and provide a medical liquid infusion apparatus capable of being safely driven and accurately transmitting medical liquids. The embodiments also provide the medical liquid infusion apparatus capable of minimizing battery consumption in manufacturing and/or distribution processes.

Embodiments of the present disclosure provide a medical liquid infusion apparatus that provides convenience to a user by being able to stop operations of internal devices such as an alarm unit and a plurality of sensor units installed therein, when necessary.

In order to achieve the above-described purpose, one aspect of the present disclosure provides a medical liquid infusion apparatus including a housing provided such that an interior thereof is at least partially open at a first time point and is sealed at a second time point later than the first time point, a needle assembly located in the housing and provided such that at least a portion thereof is discharged to an outside of the housing at a third time point later than the second time point by a user's operation, a reservoir that is sealed in the housing after the second time point, receives a medical liquid, and is fluidly connected to the needle assembly, a driving module that is sealed in the housing after the second time point, interposed between the needle assembly and the reservoir, and generates a driving force for discharging the medical liquid after the third time point, a battery module sealed in the housing after the second time point, and a control module that is sealed in the housing after the second time point, electrically connected to a transmission module and the battery module after the third time point, and configured to control the driving module.

The medical liquid infusion apparatus may further include a trigger module configured to control the driving module not to operate at least at the first time point and at the second time point.

The medical liquid infusion apparatus may further include the transmission module configured to transmit the driving force to a plunger disposed inside the reservoir, and a trigger module configured to control the transmission module not to operate at least at the first time point and at the second time point.

The control module may be configured to be disconnected from the electrically connected battery module at the first time point.

Another aspect of the present disclosure provides a medical liquid infusion apparatus including a housing provided such that an interior thereof is at least partially open at a first time point and is sealed at a second time point later than the first time point, a needle assembly accommodated in the housing and provided such that at least a portion thereof is discharged to the outside of the housing at a third time point later than the second time point, a reservoir that is accommodated in the housing, receives a medical liquid, and is fluidly connected to the needle assembly, a plurality of electronic modules that are accommodated in the housing and electrically controllable, a battery module electrically connected to the plurality of electronic modules, and an activator configured to be electrically connected to at least one of the electronic modules at the first time point.

The electronic module may include a transmission module interposed between the needle assembly and the reservoir and configured to transmit the medical liquid to the needle assembly, and the medical liquid infusion apparatus may further include a trigger module configured to control the transmission module not to operate at least at the first time point and at the second time point.

The medical liquid infusion apparatus may further include a driving module configured to transmit a driving force to a plunger disposed inside the reservoir, and a trigger module configured to control the driving module not to operate at least at the first time point and at the second time point.

The electronic module may include a communication unit electrically connected to the activator at the first time point and electrically connected to the battery module at the third time point.

The first time point may refer to a stage before shipment of the medical liquid infusion apparatus is completed. Specifically, the first time point may refer to a state before an assembly of the medical liquid infusion apparatus is completed and then an interior of the medical liquid infusion apparatus is sealed, such as waterproofing.

The second time point refers to a state in which the sealing of the medical liquid infusion apparatus is completed after the first time point. Accordingly, the second time point may also correspond to a process of distribution of the medical liquid infusion apparatus after completion of manufacturing.

The third time point refers to a time point when a use of the medical liquid infusion apparatus is started by a user, and accordingly, may include a stage of starting an operation for at least the control module and/or the driving module of the medical liquid infusion apparatus by the user.

In order to achieve the above-described purpose, another aspect of the present disclosure provides a medical liquid infusion apparatus including a first body to which a needle assembly is mounted, and a control module installed in the first body, configured to control driving of the needle assembly, and electrically connected to an internal device, wherein a fracture portion is formed to protrude outward from one side of the control module, and fractured by an external force to allow an electrical connection between the control module and the internal device to be disconnected.

The fracture portion may be formed to have a relatively narrow width in a preset region.

The medical liquid infusion apparatus may further include a housing in which the first body, the control module, and the internal device are installed, and which has an opening formed on one side thereof, and an attachment portion that covers an opening formed in the housing and is located adjacent to a user.

The medical liquid infusion apparatus may further include a fracture cover disposed to face the fracture portion and configured to open and close a path through which the external force is applied to the fracture portion.

The medical liquid infusion apparatus may further include a support portion formed to protrude from the first body toward the fracture portion and configured to support a preset region of the fracture portion.

According to embodiments of the present disclosure as described above, a medical liquid infusion apparatus and a driving method thereof according to the present disclosure can be driven and used simply and securely by a user. When the user rotates a sleeve of a needle assembly, a cannula in the needle assembly 10 is inserted into s subject, and s clutch module connects s transmission module to s driving module to drive the driving module so that the medical liquid is infused, and since driving of the driving module is started simultaneously when the user rotates the sleeve, the medical liquid infusion apparatus can be simply and safely used.

A medical liquid infusion apparatus and a driving method thereof according to the present disclosure allow a medical liquid to be quantitatively discharged since a driving module is driven in an optimized driving environment. A starter moves a position of a driving shaft before the driving module is driven, so that a contact member can be prevented from being attached to an inner surface of the driving module and interfering with the driving of the driving module. By improving storability and maintaining a precision of the medical liquid infusion apparatus, even when the medical liquid infusion apparatus is driven after being stored for a long time, the driving module can be driven smoothly and can quantitatively discharge the medical liquid to a subject.

When a user rotates a sleeve of a needle assembly, a cannula in the needle assembly is inserted into a subject to complete preparation for medical liquid infusing, and a clutch module connects a transmission module and the driving module so that a medical liquid can be injected into a needle from a reservoir, and driving of the driving module can be started simultaneously when the user rotates the sleeve. Accordingly, the user can simply rotate the needle assembly to safely start driving the medical liquid infusion apparatus.

A medical liquid infusion apparatus and a driving method thereof according to the present disclosure allow a medical liquid to be safely and quantitatively infused into a subject since structures for discharging the medical liquid are drivingly connected by a clutch unit after a cannula of a needle assembly is inserted into the subject.

A medical liquid infusion apparatus and a driving method thereof according to the present disclosure can be intuitively driven by rotation of a needle assembly, rotation directions of the needle assembly and a trigger module can be limited in one direction, and a rotation distance can be limited to a preset distance, thereby securing user safety.

The present disclosure can further improve the accuracy and reliability of a medical liquid infusion apparatus since various tests can be performed while minimizing battery consumption during manufacturing, and continuously maintaining a sanitary condition for a user.

Various devices accommodated inside a housing can be operated or tested through an activator in a state in which the medical liquid infusion apparatus is assembled and shipped, that is, in a state in which the apparatus is assembled and an entry hole is open. Accordingly, the above-described various tests can be completed without using power of a battery module mounted inside the housing. Accordingly, power consumption of the battery module can be minimized, so that the problem of power consumption during a manufacturing process or a distribution process can be minimized.

According to the present disclosure, a fracture portion formed in a control module electrically connected to internal devices, such as an alarm unit and a plurality of sensor units, can be fractured by an external force to disconnect an electrical connection of the control module and the internal devices, so that driving of the internal devices such as the alarm unit and plurality of sensor units installed internally can be stopped, when necessary, thereby providing convenience to a user.

Since the fracture portion is fractured, the present disclosure can eliminate inconvenience caused to a user by an alarm that is continuously provided in a normal or malfunctioning state of an alarm unit electrically connected to a control module.

Meanwhile, the scope of the present disclosure is not limited by these effects.

It is to be understood that both the foregoing general description and the following detailed description are exemplary illustrative and explanatory and are intended to provide further explanation of the invention as claimed.

BRIEF DESCRIPTION OF DRAWINGS

The accompanying drawings, which are included to provide a further understanding of the invention and are incorporated in and constitute a part of this specification, illustrate illustrative embodiments of the invention, and together with the description serve to explain the inventive concepts.

DETAILED DESCRIPTION

Figure 1:
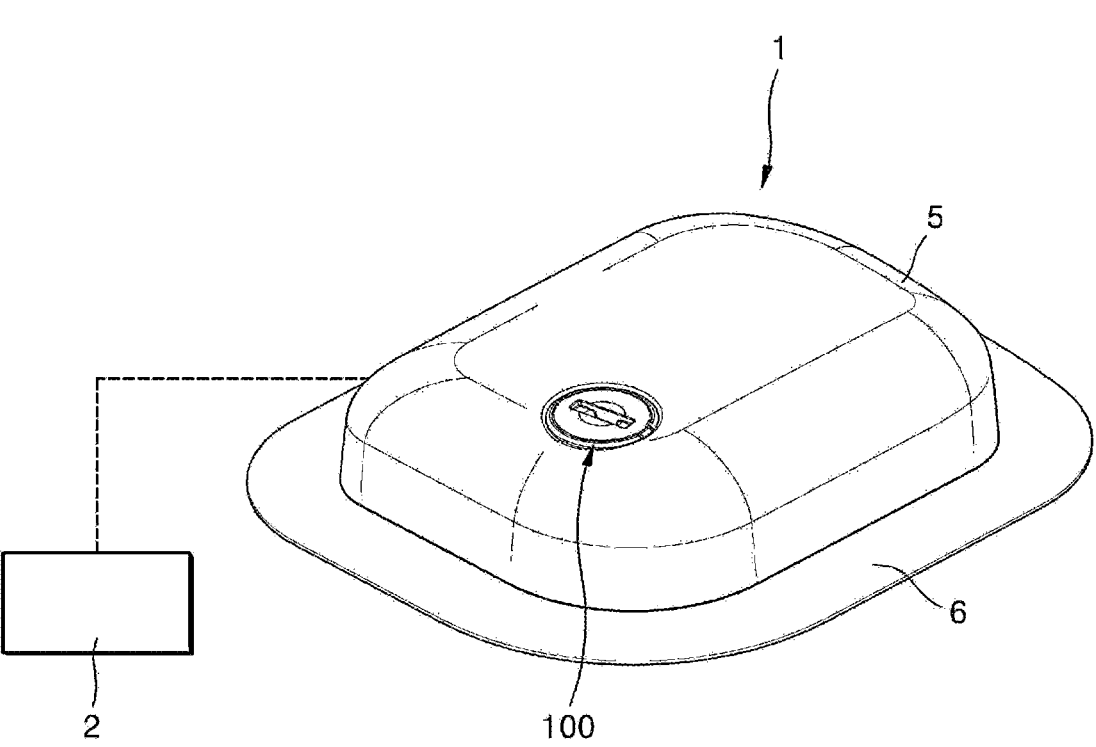
FIG. 1 is a perspective view of a medical liquid infusion system according to an embodiment.

In the following description, for the purposes of explanation, numerous specific details are set forth in order to provide a thorough understanding of various embodiments or implementations of the invention. As used herein "embodiments" and "implementations" are interchangeable words that are non-limiting examples of devices or methods employing one or more of the inventive concepts disclosed herein. It is apparent, however, that various embodiments may be practiced without these specific details or with one or more equivalent arrangements. In other instances, well-known structures and devices are shown in block diagram form in order to avoid unnecessarily obscuring various embodiments. Further, various embodiments may be different, but do not have to be exclusive. For example, specific shapes, configurations, and characteristics of an embodiment may be used or implemented in another embodiment without departing from the inventive concepts.

Unless otherwise specified, the illustrated embodiments are to be understood as providing illustrative features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

While the present disclosure is susceptible to various modifications and alternative forms, specific embodiments thereof are shown by way of example in the drawings and will herein be described in detail. Advantages and features of the present disclosure and a method of achieving the same should become clear with embodiments described below in detail with reference to the drawings. However, the present disclosure is not limited to the embodiments disclosed below, but may be implemented in various forms.

Hereinafter, the embodiments of the present disclosure will be described below in detail with reference to the accompanying drawings, and when the embodiments of the present disclosure are described with reference to the drawings, the same or corresponding components are given the same reference numerals, and repetitive descriptions thereof will be omitted.

FIG. 1 illustrates a medical liquid infusion system according to an embodiment of the present disclosure, and the medical liquid infusion system according to an embodiment may include a medical liquid infusion apparatus 1 and a medical liquid infusion control electronic apparatus 2.

Referring to FIG. 1, the medical liquid infusion apparatus 1 is attached to a subject into which a medical liquid is infused, and may quantitatively infuse a medical liquid stored therein to a user. In an optional embodiment, the medical liquid infusion apparatus 1 may be attached to a user's body through an attachment module 6 coupled to a housing 5. In addition, in another optional embodiment, the medical liquid infusion apparatus 1 may also be mounted on an animal and may infuse a medical liquid thereto.

The medical liquid infusion apparatus 1 may be used for various purposes depending on the type of medical liquid to be infused. For example, the medical liquid may include an insulin-based medical liquid for a diabetic patient, and may include a medical liquid for other pancreas, a medical liquid for heart, and other various types of medical liquids.

The medical liquid infusion apparatus 1 may be connected to the medical liquid infusion control electronic apparatus 2 connected thereto by wire or wirelessly. The user may control the medical liquid infusion apparatus 1 by operating the medical liquid infusion control electronic apparatus 2 and/or monitor a usage state of the medical liquid infusion apparatus 1. For example, the amount of medical liquid infused from the medical liquid infusion apparatus 1, the number of infusions of the medical liquid, the amount of medical liquid stored in a reservoir, user's bio information, and the like may be monitored, and based on this, the user may drive the medical liquid infusion apparatus 1.

Figure 2:
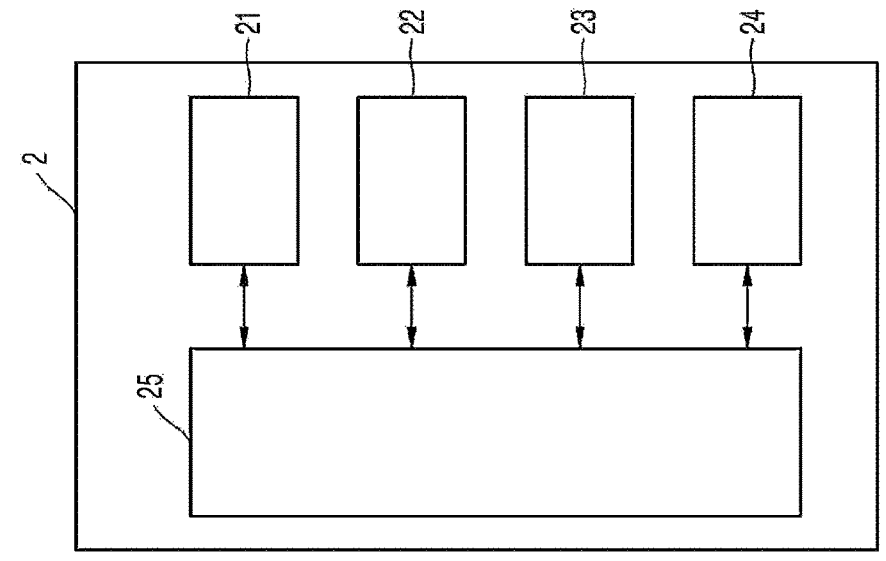
FIG. 2 is a configuration diagram of the medical liquid infusion system according to an embodiment.
Figure 2:
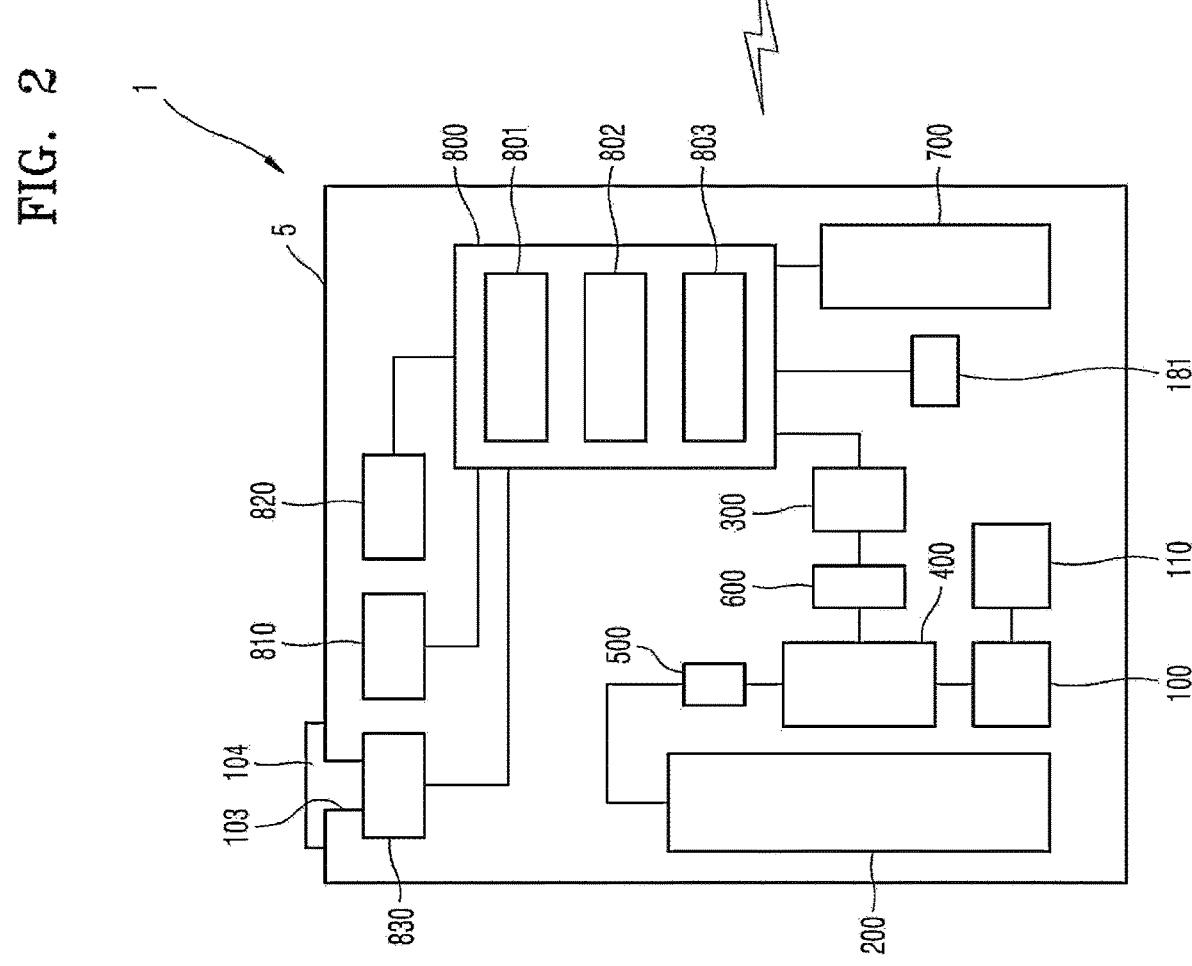

FIG. 2 is a configuration diagram of the medical liquid infusion system according to an embodiment.

In an embodiment, the medical liquid infusion apparatus 1 includes the housing 5 and a plurality of elements disposed in the housing 5. The elements disposed in the housing 5 may include a needle assembly 100, a reservoir 200, a battery module 700, a transmission module 400, and a plurality of electronic modules. According to an embodiment, the electronic modules may include a control module 800, a driving module 300, a sensing module 181, an emergency switch 810, a buzzer 820, and/or an activator 830.

The housing 5 includes an interior space, in which the various modules and/or devices described above are accommodated, and may include an entry hole 103 in at least a portion thereof so that an interior thereof may be selectively open. Such opening may be performed only during a manufacturing process, and thereafter, the entry hole 103 may sealed by a cover body 104 at a specific time point. That is, the entry hole 103 may be maintained in a sealed state, by the cover body 104, at a time point at least when the user intends to use for the first time. Accordingly, the modules and/or devices located inside the housing 5 may be sealed after this time point.

Such sealing of the housing 5 may not be a level of sealing that maintains a perfect airtightness, and may mean, for example, a degree of airtightness of a liquid rather than a degree of airtightness of gas. In addition, the sealing is not limited to the airtightness of high pressure and/or long time of the liquid, and for example, may be airtight to the extent of life waterproofing.

The reservoir 200 is disposed in the housing 5 and stores a medical liquid therein.

The needle assembly 100 is disposed in the housing 5 and transmits the medical liquid stored in the reservoir 200 into the user's body.

The transmission module 400 configured to transmit the medical liquid to the needle assembly 100 under control of the control module 800 is located between the needle assembly 100 and the reservoir 200. The transmission module 400 may include a mechanism configured to quantitatively discharge the medical liquid in the reservoir 200.

The battery module 700 is accommodated in the housing 5 and provides power to the electronic modules in the housing 5. The battery module 700 may use a primary battery or a secondary battery, and the housing 5 may not have a separate fastening structure for replacing the battery module 700 due to issues such as waterproofing and/or contamination.

The control module 800 is accommodated in the housing 5, is electrically connected to the battery module 700, and controls the medical liquid infusion apparatus 1.

The control module 800 may include a communication unit 801, a processor 802, and a switching unit 803.

The communication unit 801 is a component for communicating with the medical liquid infusion control electronic apparatus 2. The communication unit 801 may include a short-range wireless communication unit, such as, a Bluetooth communication unit, a Bluetooth Low Energy (BLE) communication unit, a Near Field Communication (NFC) communication unit, a wireless local area network (WLAN) communication unit, a Zigbee communication unit, an Infrared Data Association (IrDA) communication unit, a Wi-Fi Direct (WFD) communication unit, an Ultra-Wideband (UWB) communication unit, or an Ant+ communication unit, or a mobile communication network.

The processor 802 is a component for overall control of the medical liquid infusion apparatus 1. For example, the processor 802 may include a central processing unit (CPU), a random access memory (RAM), and/or a read only memory (ROM). Here, the ROM may be a component in which an instruction set for system booting is stored. According to an embodiment of the present disclosure, the processor 802 may be implemented as a digital signal processor (DSP) for processing a digital signal, a microprocessor, or a time controller (TCON). However, the processor is not limited thereto, and may include one or more of a central processing unit (CPU), a micro controller unit (MCU), a micro processing unit (MPU), a controller, an application processor (AP), or a communication processor (CP), an ARM processor, or may be defined by corresponding terms. In addition, the processor 802 may be implemented as a system on chip (SoC) having a built-in processing algorithm, a large scale integration (LSI), or a field programmable gate array (FPGA).

The switching unit 803 may control electrical connections of the medical liquid infusion apparatus 1. For example, the switching unit 803 may prevent the control module 800 from operating by the battery module 700 until a needle of the needle assembly 100 is inserted by a user. That is, the entire apparatus may be controlled to be maintained in an OFF state except for a minimum function until used by the user. In addition, the switching unit 803 may selectively block the sensing module 181, the emergency switch 810, the buzzer 820, the driving module 300, and the control module 800 from being electrically connected to the battery module 700 or consuming preliminary power, at a time point before used by the user, that is, after a manufacturing process and sealed by the cover body 104 and until operated by a user to initiate use. In addition, after use of the apparatus by the user, all the electronic modules of the apparatus may be allowed to be electrically connected to the battery module 700. In addition, as will described below, the electronic modules may be configured to be electrically connected to the activator 830 and to undergo various tests, even at a time point before the user uses the apparatus. According to the illustrated embodiment, the switching unit 803 is illustrated as a separate module distinct from the processor 802, but the present disclosure is not necessarily limited thereto, and the switching unit 803 may be one block of the processor 802 and may be a block including a program functioning to manage the electrical connection.

Meanwhile, the driving module 300 may be connected to the control module 800 to provide a driving force to the transmission module 400. The driving module 300 may use various pumping devices, but the driving module 300 is not necessarily limited thereto, and the driving module 300 may use driving devices such as precisely controlled motors, shape memory elements, and the like.

According to an embodiment, a clutch module 500 may be included between the transmission module 400 and the reservoir 200, and a medical liquid discharge means in the reservoir 200 may be selectively coupled to the transmission module 400 by the clutch module 500.

In addition, a trigger module 600 may be coupled to at least one of the driving module 300, the transmission module 400, and the clutch module 500, and may start or prepare for operations of the driving module 300, the transmission module 400, and/or the clutch module 500 according to a user's selection.

The sensing module 181 may include at least one sensor. The sensor may sense whether the needle assembly 100 is inserted or not and transmit the sensed information to the control module 800. According to an embodiment, the sensing module 181 may further include various other sensors. For example, the sensing module 181 may further include a sensor coupled to the reservoir 200 and configured to measure the degree of filling of the reservoir 200 with a medical liquid by a user and/or the degree of discharge of the medical liquid from the reservoir 200.

The emergency switch 810 is electrically connected to the control module 800, and is operated by a user to stop the infusion of the medical liquid when a problem occurs in the medical liquid infusion apparatus 1. The emergency switch 810 may prevent the medical liquid from being unnecessarily supplied to a patient in a dangerous situation by performing a safety function.

The buzzer 820 is electrically connected to the control module 800, and may be configured to sound in a crisis situation or the like to call attention to the user.

The activator 830 may be configured to be electrically connected to at least one of the electronic modules in the housing 5 when the entry hole 103 of the housing 5 is open.

Specifically, the activator 830 may be electrically connected to the control module 800. Accordingly, an external device may be electrically connected to the control module 800 at a time point when the entry hole 103 of the housing 5 is open, and may also be electrically connected to various electronic modules, which are electrically connected to the control module 800, through the control module 800. The time point when the entry hole 103 is open may be a state in which the power is cut off from the battery module 700, and in this state, switching, testing, and/or diagnosis of various electronic modules accommodated in the housing 5 may be performed through the activator 830.

According to FIG. 2, although the activator 830 is illustrated as being electrically connected to the control module 800 and electrically in communication with other electronic modules through the control module 800, the present disclosure is not necessarily limited thereto, and although not shown in the drawing, the activator 830 may be directly connected to other electronic modules, for example, the driving module 300, the sensing module 181, the emergency switch 810, and/or the buzzer 820 used in the housing 5.

Optionally, the activator 830 may be electrically connected to the battery module 700 so as to be directly connected thereto. This may allow the battery module 700 to be controlled and/or supplied with power from the outside through the activator 830 from the time point when the entry hole 103 is open. In addition, the activator 830 may also be used for grounding.

The medical liquid infusion apparatus 1 is a medical apparatus that requires a very high level of waterproof performance, and is difficult to be disassembled and used again once assembled for reasons such as the need to ensure that distinct traces of disassembly necessarily remain when it is arbitrarily disassembled by the user. In addition, the medical liquid infusion apparatus 1 is sometimes driven by disposable batteries that are never reused, and, in some cases, has a long expiration date of 12 months or more. As such, it is necessary to minimize battery consumption of the medical liquid infusion apparatus 1 during production or distribution and maintain the performance thereof not to be degraded.

Accordingly, there is a limitation in using a built-in battery to test functions of various parts of the medical liquid infusion apparatus 1 until the medical liquid infusion apparatus 1 is assembled and shipped. That is, in this case, it is necessary to minimize battery consumption during various tests of the medical liquid infusion apparatus 1, and to ensure that the medical liquid infusion apparatus 1 can be maintained in a stand-by state with minimal power until a user acquires the medical liquid infusion apparatus 1 and starts operation of the medical liquid infusion apparatus 1. For example, it is possible to maintain only monitoring power sufficient to turn on the switch when the user injects a certain amount of medical liquid into the reservoir 200.

In this state, since the activator 830 is electrically connected to the control module 800, the electronic module, and/or the battery module 700 as described above, various tests of the medical liquid infusion apparatus 1 may be performed without using power from the battery module 700 by connecting an external power source, test device, or the like to the activator 830 in a state in which the medical liquid infusion apparatus is assembled and the entry hole 103 is open.

More specifically, external power may be supplied to the medical liquid infusion apparatus 1 through the activator 830. In this case, the activator 830 may include at least two wiring patterns.

Optionally, an external test device may be connected through the activator 830 to test various devices including the driving module 300.

Optionally, a test operation of the driving module 300 may be performed through the activator 830.

The activator 830 may be exposed to the outside in a state before the apparatus is assembled and shipped, that is, in a state in which the apparatus is assembled and the entry hole 103 is open. With the activator thus exposed, the various devices accommodated in the housing 5 may be test operated as described above. Thereafter, the entry hole 103 may be sealed through the cover body 104 to complete the waterproofing of the housing 5. Since various tests may be performed through the activator 830 as described above, the above-described various tests may be completed without using the power of the battery module 700 mounted inside the housing 5. This may minimize power consumption of the battery module 700, so that the problem of power consumption during a manufacturing process or a distribution process may be minimized.

Meanwhile, the medical liquid infusion control electronic apparatus 2 may include a communication terminal that allows an application to be utilized in a wired or wireless communication environment. Here, the medical liquid infusion control electronic apparatus 2 may be a user's portable terminal. In more detail, the medical liquid infusion control electronic apparatus 2 may include a computer (e.g., desktop, laptop, tablet, or the like), a media computing platform (e.g., cable, satellite set-top box, digital video recorder), a handheld computing device (e.g., personal digital assistant (PDA), e-mail client, or the like), a mobile phone in any form, a form of a wearable device that can be attached or mounted on the user's body, or any form of another kind of computing or communication platform, but the present disclosure is not limited thereto.

The medical liquid infusion control electronic apparatus 2 may include a processor 25, a communication unit 21, an input unit 22, an output unit 23, and a storage unit 24.

The processor 25 is a component for overall control of the medical liquid infusion apparatus 1 and/or the medical liquid infusion control electronic apparatus 2. Specifically, the processor 25 controls overall operations of the medical liquid infusion apparatus 1 and/or the medical liquid infusion control electronic apparatus 2 by using various programs stored in the storage unit 24 of the medical liquid infusion control electronic apparatus 2. For example, the processor 25 may include a CPU, a RAM, and/or a ROM. Here, the ROM is a component in which an instruction set for system booting is stored, and the CPU copies an operating system (O/S) stored in the memory of the medical liquid infusion control electronic apparatus 2 into the RAM according to an instruction stored in the ROM, and boots the system by executing the O/S. When the booting is completed, the CPU may copy and execute various applications stored in the storage unit 24 to the RAM to perform various operations. Although it has been described above that the medical liquid infusion control electronic apparatus 2 includes only one CPU, the medical liquid infusion control electronic apparatus 2 may be implemented with a plurality of CPUs (or a digital signal processors (DSPs), system on chips (SoCs), or the like).

According to an embodiment of the present disclosure, the processor 25 may be implemented as a digital signal processor (DSP) for processing a digital signal, a microprocessor, or a time controller (TCON). However, the processor is not limited thereto, and may include one or more of a central processing unit (CPU), a micro controller unit (MCU), a micro processing unit (MPU), a controller, an application processor (AP), or a communication processor (CP), an ARM processor, or may be defined by corresponding terms In addition, the processor 25 may be implemented as a system on chip (SoC) having a built-in processing algorithm, a large scale integration (LSI), or a field programmable gate array (FPGA).

The medical liquid infusion control electronic apparatus 2 may include the storage unit 24 for storing a program for processing or controlling the processor 25 and/or various data for operation of the program. The storage unit 24 may store a plurality of application programs (or applications) driven in the medical liquid infusion apparatus 1 and/or the medical liquid infusion control electronic apparatus 2, and data and instructions for the operation of the medical liquid infusion apparatus 1 and/or the medical liquid infusion control electronic apparatus 2. At least some of these application programs may be downloaded from an external server through wireless communication. In addition, at least some of these application programs may be present on the medical liquid infusion control electronic apparatus 2 from the time of shipment for a basic function of the medical liquid infusion apparatus 1 and/or the medical liquid infusion control electronic apparatus 2. The application program may be stored in a storage medium and driven, by the processor 25, to perform an operation (or function) of the medical liquid infusion apparatus 1 and/or the medical liquid infusion control electronic apparatus 2.

The communication unit 21 is a component for transmitting and receiving data to and from devices such as the medical liquid infusion apparatus 1 and/or an external device, that is, a server, another user terminal, and the like. The communication unit 21 may include a short-range wireless communication unit, such as, a Bluetooth communication unit, a Bluetooth Low Energy (BLE) communication unit, a Near Field Communication (NFC) communication unit, a wireless local area network (WLAN) communication unit, a Zigbee communication unit, an Infrared Data Association (IrDA) communication unit, a Wi-Fi Direct (WFD) communication unit, an Ultra-Wideband (UWB) communication unit, or an Ant+ communication unit, or a mobile communication network.

The input unit 22 may include a user interface for inputting various information to the medical liquid infusion control electronic apparatus 2.

The output unit 23 may display medical liquid infusion logic processed by the processor 25, medical liquid infusion status, blood glucose level status, effects, and the like. According to an embodiment of the present disclosure, the output unit 23 may display a user interface according to a user input inputted through the input unit 22. The output unit 23 may output stored graphic data, visual data, auditory data, and vibration data under control of the storage unit 24.

The output unit 23 may be implemented as various types of display panels. For example, the display panel may be implemented with various display technologies such as Liquid Crystal Display (LCD), Organic Light Emitting Diodes (OLED), Light-Emitting Diode (LED), Liquid Crystal on Silicon (LcoS), or DLP (Digital Light Processing). In addition, the output unit 23 may be coupled to at least one of a front region, a side region, and a rear region of the display panel, in the form of a flexible display.

The output unit 23 may be implemented as a touch screen having a layer structure. The touch screen may have a function of detecting not only a display function but also a touch input position, a touched area, and even a touch input pressure, and may also have a function of detecting not only a real-touch but also a proximity touch.

The medical liquid infusion control electronic apparatus 2 may include the storage unit 24 and the communication unit 21 therein. The medical liquid infusion control electronic apparatus 2 may not include at least one of the processor 25, the input unit 22, and the output unit 23, and may be electrically connected to at least one of a processor 25, an input unit 22, and an output unit 23 provided in a remote apparatus.

According to FIGS. 1 and 2, the medical liquid infusion control electronic apparatus 2 is illustrated as being a single device, but the present disclosure is not necessarily limited thereto, and may include a plurality of devices capable of communicating with the medical liquid infusion apparatus 1.

Figure 3:
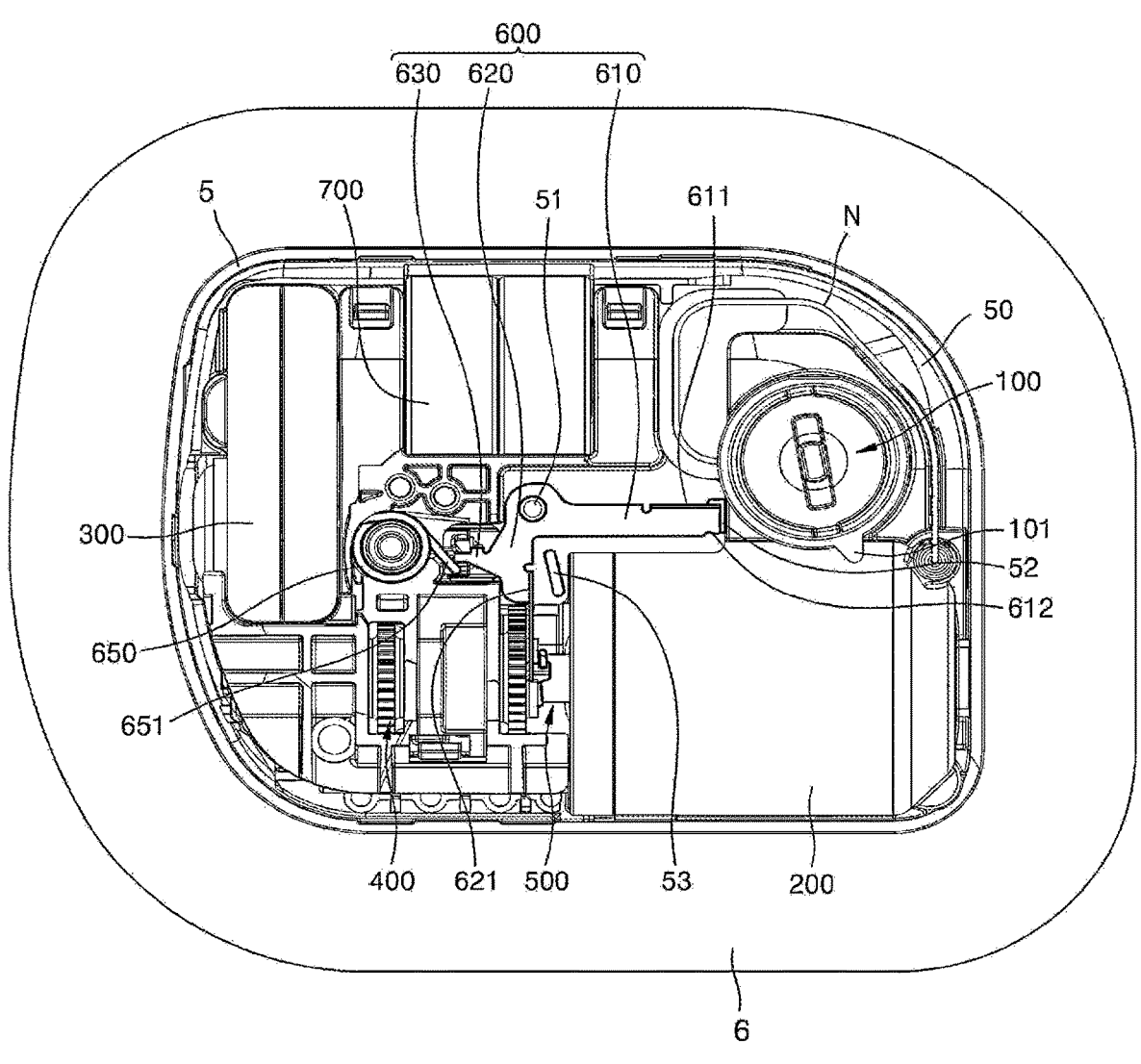
FIG. 3 is a plan view illustrating a more specific embodiment of the medical liquid infusion apparatus of FIG. 2.
Figure 4:
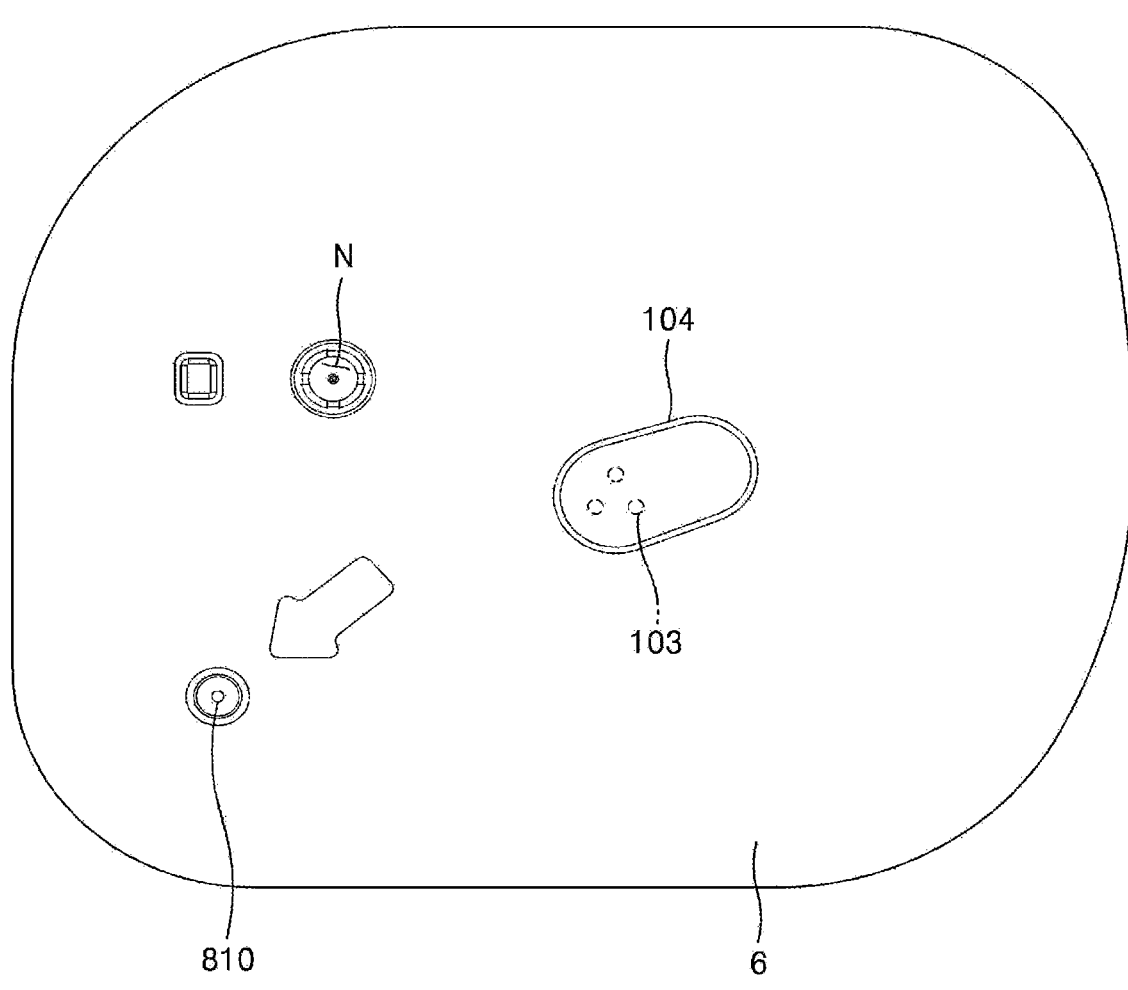
FIG. 4 is a bottom view illustrating a more specific embodiment of the medical liquid infusion apparatus of FIG. 2.

FIG. 3 is a plan view illustrating a more specific embodiment of the medical liquid infusion apparatus 1 of FIG. 2, and FIG. 4 is a bottom view thereof.

Referring to FIG. 3, an embodiment of the medical liquid infusion apparatus 1 may include a base body 50, a needle assembly 100, a reservoir 200, a driving module 300, a transmission module 400, a clutch module 500, and a battery module 700.

The base body 50 forms a basic frame of the housing 5 and is mounted in an inner space of the housing 5. The base body 50 may be provided in plural. In another embodiment, the base body may be formed as an integral single frame.

The medical liquid infusion apparatus 1 according to the embodiment shown in FIG. 3 may optionally further include a trigger module 600.

The base body 50 may provide a space in which the trigger module 600 may pivot. The base body 50 may support the trigger module 600, and the trigger module 600 may pivot around a pivot shaft 51 protruding from the base body 50.

The base body 50 may include a stopper that limits a pivot distance of the trigger module 600. A plurality of stoppers may be provided, and may limit a movement distance of the trigger module 600 such that the trigger module 600 pivots to a preset point. According to an embodiment, the stoppers may include a first stopper 52 and a second stopper 53.

The first stopper 52 protrudes upward from the base body 50 and is disposed adjacent to the needle assembly 100. The first stopper 52 is disposed to be in contact with a first end 610 of the trigger module 600, and may limit a rotation direction and a rotation distance of the first end 610 so that the first end 610 does not rotate in an opposite direction after rotating in one direction. The first stopper 52 may have a sidewall that limits a pivoting direction of the trigger module 600.

The second stopper 53 is disposed adjacent to the reservoir 200, the transmission module 400, and the clutch module 500. The second stopper 53 may be disposed to protrude upward from the base body 50 and may limit a movement distance of a second end 620 of the trigger module 600. In an embodiment, the second stopper 53 includes a longitudinal extension line that may pass through a center of the pivot shaft 51.

An embodiment of the trigger module 600 is not necessarily limited to the above-described embodiment and, of course, various devices may be used, which can start operation of at least one of the driving module 300, the transmission module 400, and the clutch module 500 according to the intention of a user.

An attachment portion 6 is provided on a bottom surface of the medical liquid infusion apparatus 1, and may be attached to the user's skin. A needle N may be exposed on the bottom surface, and at a stage before the user initially uses the device, a hole through which the needle N is exposed may be coupled to a separate cover member (not shown) so that a sealed state blocked from the outside may be maintained. In addition, optionally, an emergency switch 810 may be exposed on the bottom surface, so that the user may stop the operation in a dangerous situation by pressing the switch 810. The emergency switch 810 may be configured to be sealed so that external moisture cannot penetrate thereto.

An entry hole 103 may be formed in the bottom surface of the medical liquid infusion apparatus 1, and the entry hole 103 is not necessarily limited to one, and a plurality of entry holes 103 may be formed. In addition, in a stage where the medical liquid infusion apparatus 1 is released to the market, the entry hole 103 may be covered by the cover body 104 so that the inside remains sealed. A bonding film for sealing the interior of the housing may be used as the cover body 104, and according to an embodiment, a film that prevents the communication of liquids and allows the communication of gases may be used. According to a specific embodiment, a Tyvek material or a Gore-Tex material may be used as the cover body 104. In addition, the cover body 104 may have a structure that simultaneously covers the plurality of entry holes 103, but is not necessarily limited thereto, and may have a structure attached to each entry hole 103.

Figure 5A:
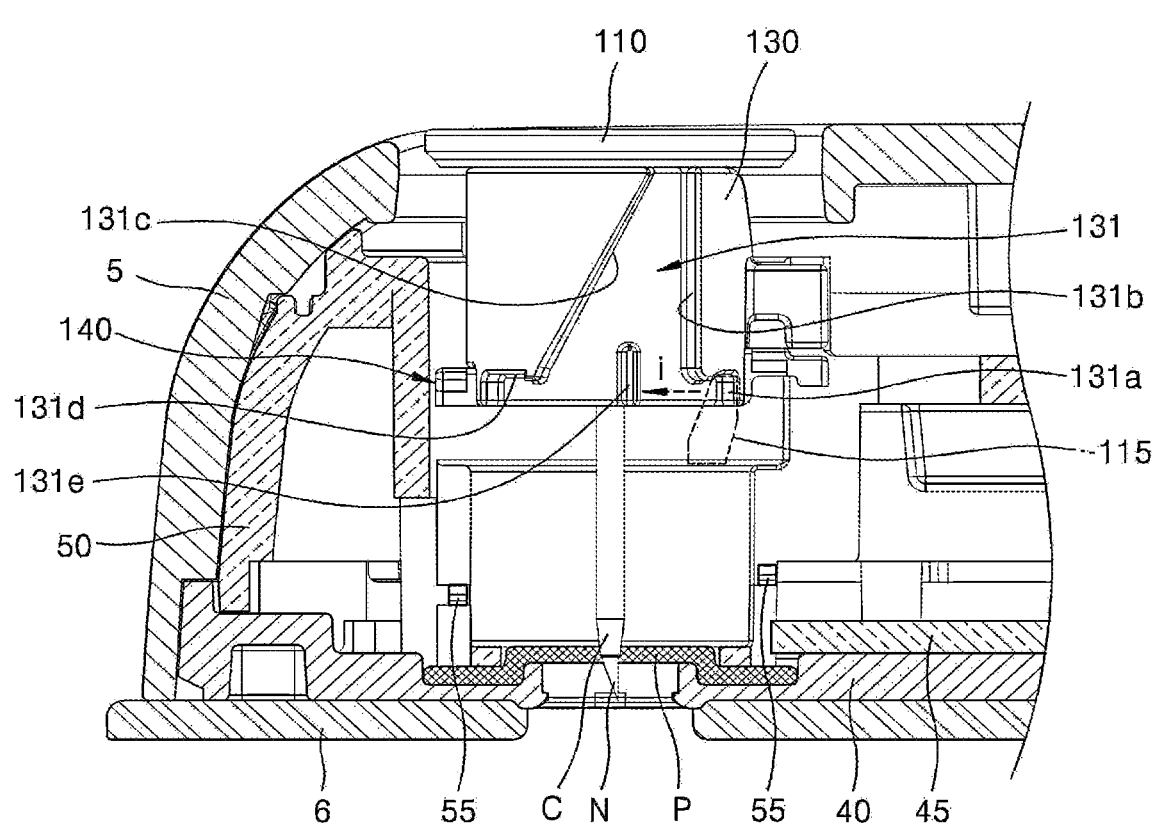
FIGS. 5A to 5C are cross-sectional views illustrating driving of a needle assembly according to an embodiment.
Figure 5B:
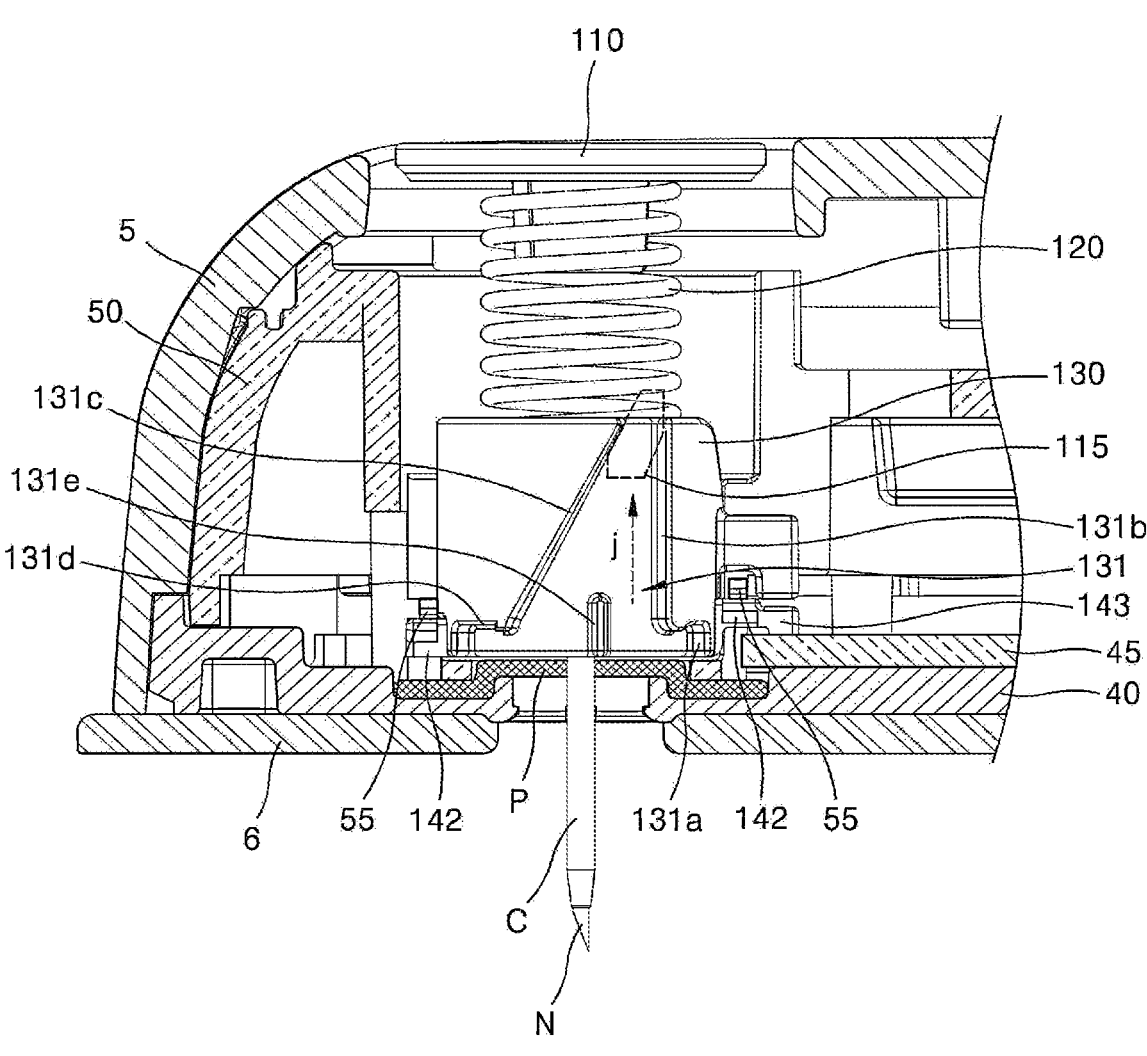
Figure 5C:
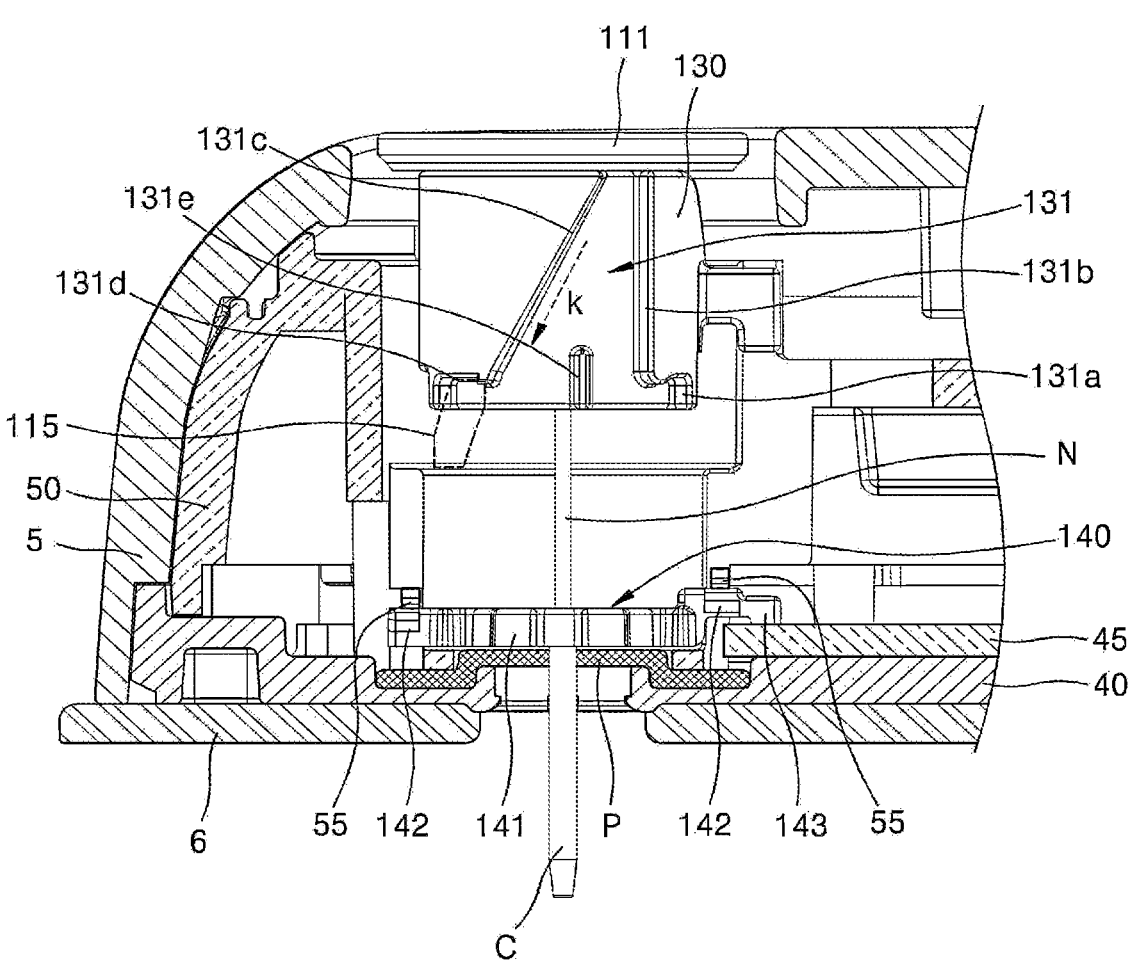

FIGS. 5A to 5C are cross-sectional views illustrating driving of the needle assembly 100 according to an embodiment.

Referring to FIGS. 5A to 5C, the needle assembly 100 may be mounted to the base body 50. The needle assembly 100 is rotated so that the needle N and/or a cannula C may move in an axial direction. The needle assembly 100 may include a sleeve 110, an elastic member 120, a first holder 130, a second holder 140, the needle N, the cannula C, and a patch P.

The sleeve 110 forms an outer appearance of the needle assembly 100 and may be rotated around a longitudinal direction as a central axis. The elastic member 120 may be disposed inside the sleeve 110 so that the sleeve 110 may receive an expansion force from the elastic member 120.

Optionally, according to an embodiment, a knob 101 may be disposed on an outer side of the sleeve 110. When the needle assembly 100 rotates, the knob 101 may press the first end 610 of the trigger module 600 to pivot the trigger module 600.

A moving protrusion 115 may be disposed on an inner surface of the sleeve 110. The moving protrusion 115 may move along a guide groove 131 disposed on an outer circumferential surface of the first holder 130. When the sleeve 110 rotates, the moving protrusion 115 may move along sidewalls of the guide groove 131 so that the first holder 130 may be raised or lowered.

The elastic member 120 may be disposed between the sleeve 110 and the first holder 130. When the elastic member 120 expands, the first holder 130 may be moved downward. In addition, when the first holder 130 moves in an upward direction, the elastic member 120 may be compressed.

The first holder 130 may support the needle N. Since the needle N is inserted and fixed to one side of the first holder 130, when the first holder 130 moves in the axial direction, the needle N is also moved together with the first holder 130. The first holder 130 is disposed in an inner space of the sleeve 110, and the elastic member 120 is disposed above the first holder 130.

The first holder 130 may include the guide groove 131 on an outer surface thereof. The guide groove 131 may guide the movement of the moving protrusion 115. When the sleeve 110 rotates, the moving protrusion 115 is moved to a preset path formed by the guide groove 131 so that the first holder 130 may be raised or lowered.

The guide groove 131 may include a first stopping groove 131a, a lifting groove 131b, an inclined groove 131c, a second stopping groove 131d, and a movement limiting groove 131e. The first stopping groove 131a is a groove in which the moving protrusion 115 is initially located, and the elastic member 120 remains in a contracted state when the moving protrusion 115 is located in the first stopping groove 131a. The lifting groove 131b extends in the longitudinal direction of the first holder 130. When the elastic member 120 expands, the first holder 130 is lowered and the moving protrusion 115 moves along the lifting groove 131b. The inclined groove 131c extends to have a preset inclination. When the moving protrusion 115 moves along the inclined groove 131c, the elastic member 120 is contracted again and the first holder 130 is raised again. The second stopping groove 131d is a groove in which the moving protrusion 115 returns to its initial position, and in this case, the elastic member 120 remains in a contracted state again when the moving protrusion 115 is located in the second stopping groove 131d.

The second holder 140 is disposed to face one side of the first holder 130 and may support the cannula C. The second holder 140 is formed of a flexible material, and when an external force is applied, the shape of the second holder 140 may be instantaneously deformed.

The second holder 140 maintains contact with the first holder 130 at positions of FIGS. 5A and 5B, but when the elastic member 120 is contracted again as shown in FIG. 5C, the second holder 140 is separated from the first holder 130 and fixed to the base body 50.

The cannula C may be inserted into a center of a central body 141, and the needle N may be selectively coupled according to the movement of the first holder 130. The central body 141 may be in contact with a lower end of the first holder 130.

A locking protrusion 142 may protrude outward from the central body 141 and may be formed to be flexible. The locking protrusion 142 may be provided in plural. Referring to FIG. 5C, the locking protrusion 142 is fixed to a ledge part 55 when the second holder 140 is lowered, so that the first holder 130 may be fixed to the base body 50 even when the first holder 130 is raised again.

A sensor 143 may be disposed on one side of the locking protrusion 142. However, the sensor 143 is not limited thereto, and may be disposed on an outer surface of the central body 141. The sensor 143 may detect whether the cannula C is accurately inserted into the user's skin. The sensor 143 may sense a contact between the second holder 140 and a base 40.

In detail, since the second holder 140 moves over the ledge part 55 when the second holder 140 moves downward, the sensor 143 may measure whether the second holder 140 is in contact with a contact part 45 disposed above the base 40. The sensor 143 is formed of a conductive material, and thus, an electrical signal is generated when the second holder 140 is in contact with the contact part 45, and a control module (not shown) may check whether the second holder 140 is inserted.

Since the needle N is fixed to the first holder 130, the needle N may be inserted into or removed from the cannula C by moving the first holder 130 in the axial direction. One end of the needle N may be connected to the reservoir 200 so that a medical liquid may be transmitted therethrough, and the other end thereof may be inserted into the cannula C and may move along the cannula C.

Since the cannula C is fixed to the second holder 140, the cannula C may be inserted into the user's skin by moving the second holder 140 in the axial direction. The cannula C has a tube shape capable of accommodating the needle N, so that the medical liquid discharged from the needle N may be infused into the user.

The patch P is supported on the base 40 and may fix the position of the cannula C. Since an end portion of the cannula C is supported by the patch P, separation of the cannula C during storage or during movement may be prevented.

As shown in FIG. 5A, the needle N and the cannula C are initially disposed inside the needle assembly 100. When the user firstly rotates the sleeve 110, the moving protrusion 115 is moved in a direction of i over the first stopping groove 131a.

As shown in FIG. 5B, the first holder 130 is lowered by the expansion force of the elastic member 120. The moving protrusion 115 is not actually moved in the axial direction, but moved in a direction of j along the lifting groove 131b relative to the first holder 130 by the lowering of the first holder 130. The first holder 130 and the second holder 140 are lowered together, and the needle N and the cannula C pass through the patch P and are inserted into a subject.

As shown in FIG. 5C, when the user secondarily rotates the sleeve 110, the moving protrusion 115 is moved in a direction of k along the inclined groove 131c and is inserted into the second stopping groove 131d. The second holder 140 is fixed by the ledge part 55, but the first holder 130 is raised according to the rotation of the sleeve 110, and the elastic member 120 is re-contracted by the rise of the first holder 130.

At this time, the cannula C maintains the state of being inserted into the user's skin, but the needle N is raised and separated from the subject. However, the cannula C and the needle N are fluidly connected so that the medical liquid injected from the reservoir 200 may be infused to the user through the needle N and the cannula C.

The medical liquid infusion apparatus 1 may insert the cannula C into the subject and start the infusion of the medical liquid as the user simply rotates the sleeve 110. In the medical liquid infusion apparatus 1, as the user firstly rotates the sleeve 110, the cannula C may be inserted into the subject, and the knob 101 press the trigger module 600 to drive the driving module 300. More preferably, as shown in FIG. 5C, in a state in which the needle N is withdrawn from the subject and only the cannula C is inserted into the subject, the knob 101 presses the trigger module 600 and drives the driving module 300 to transmit a medical liquid, and the medical liquid may be quantitatively discharged from the reservoir 200. Thus, the user may conveniently and stably use the medical liquid infusion apparatus 1.

Referring to FIG. 3 again, the reservoir 200 is mounted to the base body 50 and is connected to the needle assembly 100. A plunger 230 (in FIG. 7) linearly moves inside the reservoir 200 to discharge the medical liquid to the needle N.

The driving module 300 may generate a driving force and transmit the driving force to the transmission module 400. The driving force transmitted to the transmission module 400 linearly moves the plunger 230 in the reservoir 200 to discharge the medical liquid.

All types of devices having a medical liquid suction force and a medical liquid discharge force by electricity may be used as the driving module 300. For example, all types of pumps such as a mechanical displacement type micropump and an electromagnetic motion type micropump may be used. The mechanical displacement type micropump is a pump that uses solid or fluid motion such as a gear or diaphragm to generate a pressure difference to induce fluid flow, and includes a diaphragm displacement pump, a fluid displacement pump, a rotary pump, and the like. The electromagnetic motion micropump is a pump that directly uses electrical or magnetic energy for fluid movement, and may include an electro-hydrodynamic pump (EHD), an electro-osmotic pump, a magneto-hydrodynamic pump, an electro-wetting pump, and the like.

When parts in the transmission module 400 are engaged to each other by the clutch module 500, the driving module 300 rotates a driving wheel 420 of the transmission module 400, and a rod linearly moves by the rotation of the driving wheel 420 to move the plunger 230 in the reservoir 200.

Figure 6:
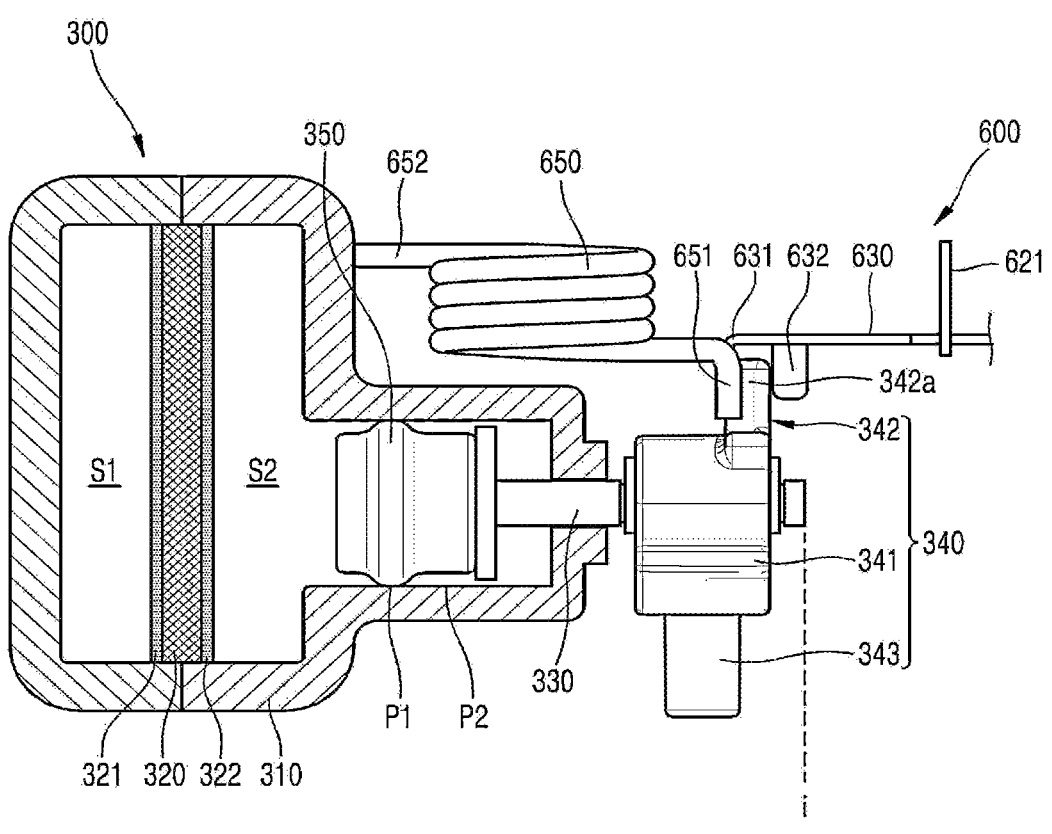
FIG. 6 is a cross-sectional view of a driving module according to an embodiment.

FIG. 6 is a cross-sectional view of the driving module 300 according to an embodiment.

The driving module 300 may include a membrane 320 disposed inside a cover 310. The membrane 320 may partition an inner space of the driving module 300 into a first space S1 and a second space S2. In the driving module 300, a driving shaft 330 may be linearly moved by changes in volumes of the first space S1 and the second space S2.

The membrane 320 may have a porous structure through which a fluid and ions may move. The membrane 320 may be, for example, a frit-type membrane that is fabricated by sintering spherical silica with heat. For example, the spherical silica used to form the membrane may have a diameter of about 20 nm to about 500 nm, in particular, a diameter of about 30 nm to about 300 nm, and in more particular, a diameter of about 40 nm to about 200 nm. When the diameter of the spherical silica satisfies the above range, a pressure caused by a first fluid passing through the membrane 320, that is, a sufficient pressure to move the driving shaft 330, may be generated.

In the above-described embodiment, the membrane 320 includes the spherical silica, but the membrane 320 is not limited thereto. In another embodiment, a kind of a material included in the membrane 320 is not particularly limited as long as the material is a material that may cause an electrokinetic phenomenon due to zeta potential, for example, porous silica or porous alumina.

The membrane 320 may have a thickness of about 20 μm to about 10 mm, in particular, about 300 μm to about 5 mm, and in more particular, about 1000 μm to about 4 mm.

A first electrode body 321 and a second electrode body 322 are respectively arranged on opposite sides of the membrane 320. Each of the first electrode body 321 and the second electrode body 322 may be in the form a porous plate.

The porous plates may be disposed to be in contact with both main surfaces of the membrane 320, respectively. The porous plate may effectively move a fluid and ions due to the porous structure. The porous plate may have a structure in which an electrochemical reaction material is formed on a porous base layer. The electrochemical reaction material may be formed by being electrodeposited or coated on the porous base layer by a method such as electroless plating, vacuum deposition, coating, sol-gel process, or the like.

The porous base layer may have a pore size of about 0.1 μm to about 500μ, in particular, about 5 μm to about 300μ, and in more particular about 10 μm to about 200 μm. When the pore size of the porous base layer satisfies the above range, the fluid and the ions may be effectively moved, thereby improving stability, lifespan characteristics, and efficiency of the driving module 300.

The driving shaft 330 may be disposed on one side of the cover 310 and may linearly move according to changes in volumes of the first space S1 and the second space S2. When an oxidation/reduction reaction occurs in the first electrode body 321 and the second electrode body 322, a volume change is generated in the first space S1 and the second space S2 by products (e.g., hydrogen ions and water) produced by the oxidation/reduction reaction. The changes in volumes of the first space S1 and the second space S2 may press the driving shaft 330 so that the driving shaft may linearly move.

Referring to FIG. 6, a moving terminal 340 is disposed at an end portion of the driving shaft 330, and may transmit the driving force generated by the driving module 300 to the transmission module 400. The moving terminal 340 may include a body 341 into which the driving shaft 330 is inserted, a guide protrusion 342 protruding upward from the body 341, and a connection shaft 343 connected to the transmission module 400.

A sidewall of the guide protrusion 342, which faces the trigger module 600 or a starter 650, may be formed to be inclined. An inclined surface 342a may have a predetermined angle along the driving shaft 330.

The connection shaft 343 is connected to a connector (not shown) of the transmission module 400. The connection shaft 343 linearly moves by the linear movement of the driving shaft 330, and may move the connector to drive the driving wheel 420.

A contact member 350 may be mounted on an outer side of the driving shaft 330. The inner space of the driving module 300, for example, the second space S2 defined by an inner surface of the cover 310 and one side surface of the driving shaft 330, is a sealed space and has a fluid therein. The contact member 350 may prevent the fluid from leaking into a gap between the inner surface of the cover 310 and the driving shaft 330.

The contact member 350 is formed of a material having a predetermined elasticity to tightly seal the gap between the inner surface of the cover 310 and the driving shaft 330. In an embodiment, the contact member 350 may be formed of a silicone-based and/or rubber-based material.

Figure 7:
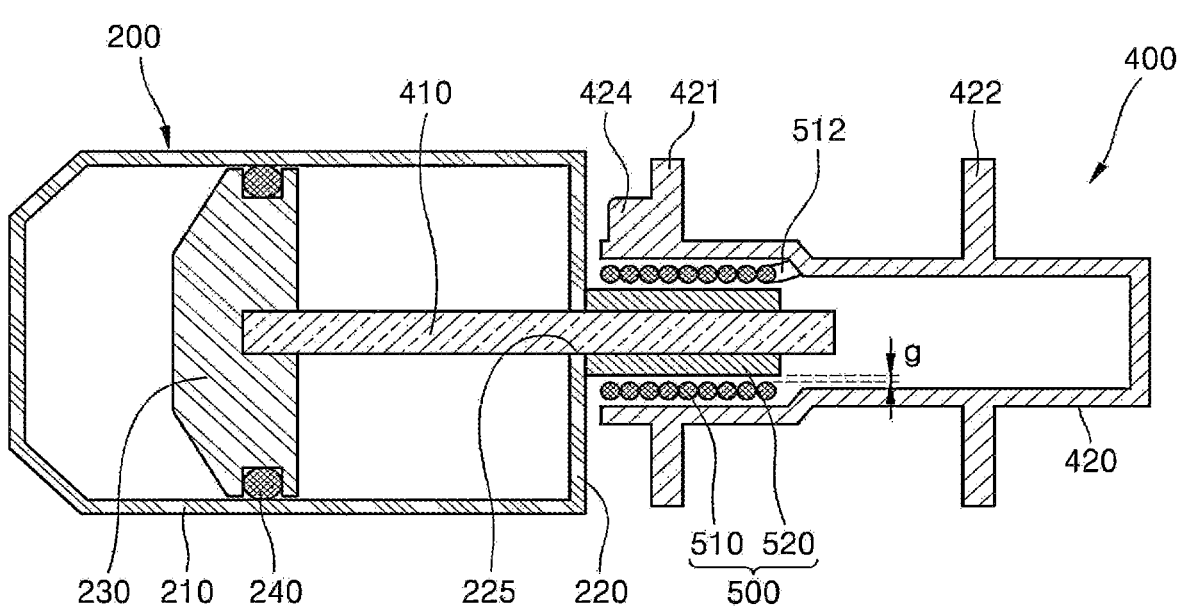
FIG. 7 is a cross-sectional view illustrating a structure of an embodiment of a reservoir and a transmission module.
Figure 8:
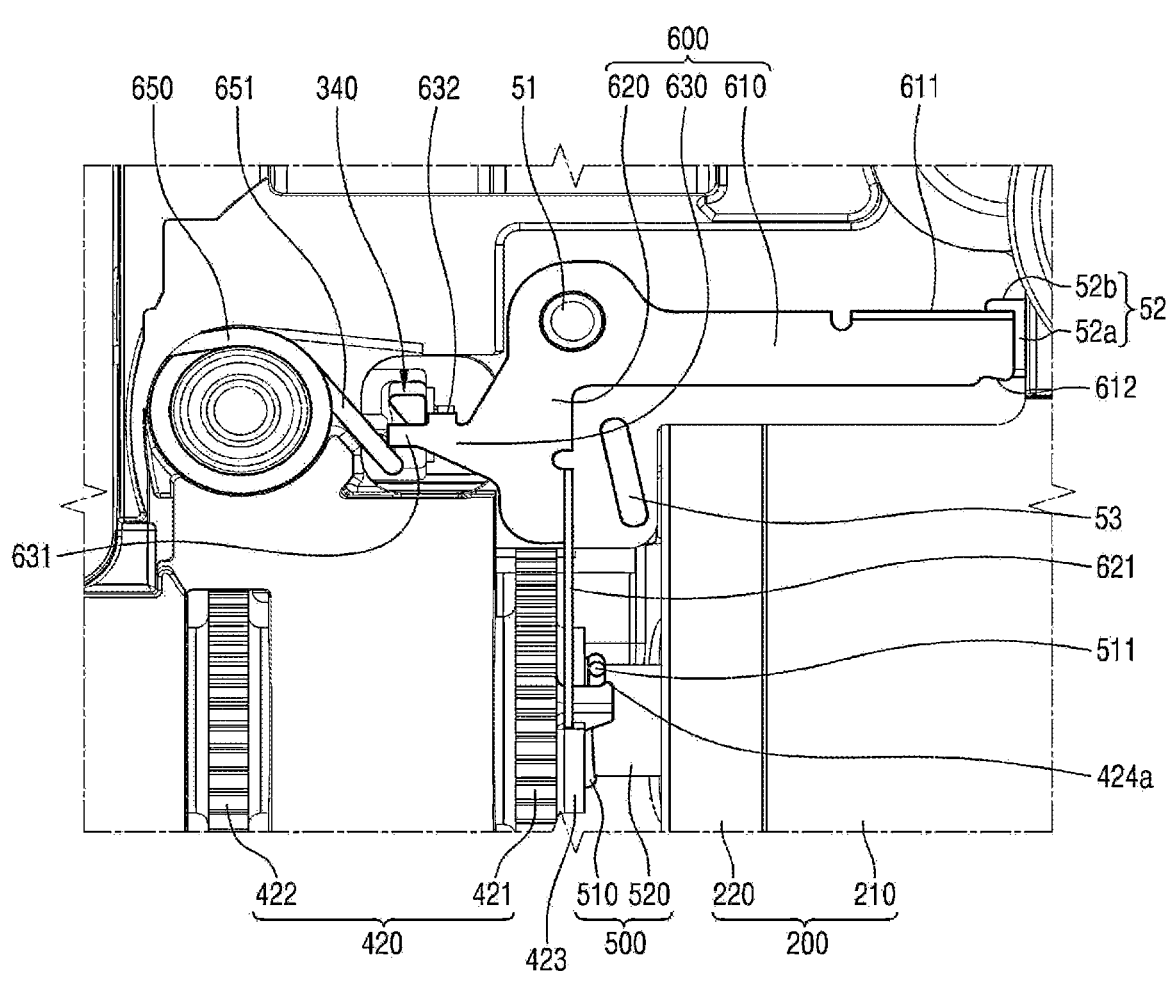
FIG. 8 is a plan view of a portion of the embodiment of the reservoir and the transmission module.

FIG. 7 is a cross-sectional view illustrating a structure of an embodiment of the reservoir 200 and the transmission module 400, and FIG. 8 is a plan view of a portion thereof.

The transmission module 400 is installed between the driving module 300 and the reservoir 200, and may move a plunger 230 disposed in the reservoir 200 by the driving force generated by the driving module 300. However, the transmission module 400 may move the plunger 230 only when a rod 410 and the driving wheel 420 are coupled by the clutch module 500.

The rod 410 has one end connected to the plunger 230 and extends in one direction. The driving wheel 420 is drivably connected to the driving module 300, and may be rotated by driving of the driving module 300. The driving wheel 420 includes a first connection terminal 421 and a second connection terminal 422, and may have a space therein in which the rod may move. At least one of the first connection terminal 421 and the second connection terminal 422 is always drivably connected to the driving module 300 by a connector, so that the driving wheel 420 may be rotated by the driving of the driving module 300.

In an embodiment, the first connection terminal 421 and the second connection terminal 422 may each have a shape of a gear tooth. The connector (not shown) connected to the driving module 300 may press the gear tooth so that the driving wheel 420 rotates.

The driving wheel 420 may include a hub 423 protruding from the first connection terminal 421. Referring to FIG. 8, the hub 423 may protrude to a predetermined height. The hub 423 may form a space into which a second flange 621 of the trigger module 600 may be inserted.

The driving wheel 420 includes a first supporter 424 protruding from one side to support one end portion 511 of a coupler 510. As shown in FIG. 8, the first supporter 424 may be disposed on one surface of the driving wheel 420 to support the one end portion 511 of the coupler 510 such that a diameter of the coupler 510 remains expanded.

In an optional embodiment, the first supporter 424 may include a protrusion protruding from an end portion thereof to prevent the one end portion 511 of the coupler 510 from being separated.

When the coupler 510 is separated from the first supporter 424, the coupler 510 grips an inserter 520 while being reduced in diameter. Since the coupler 510 is contracted to a set radius, a predetermined gripping force may be provided to the inserter 520.

The clutch module 500 may drivingly connect the driving module 300 and the transmission module 400. The clutch module 500 is disposed between the rod 410 and the driving wheel 420, and may include the inserter 520 and the coupler 510.

The inserter 520 may be disposed such that the rod 410 is inserted into at least a portion of the inserter 520. The inserter 520 is disposed to cover an outer side of the rod. The inserter 520 may connect the driving module 300 and the rod 410 according to the operation of the coupler 510.

In an embodiment, the rod and the inserter 520 may have a screw shape and a screw thread shape, respectively. A screw thread may be formed on an outer circumferential surface of the rod, and a screw thread may be formed on an inner circumferential surface of the inserter 520, and thus the rod and the inserter 520 may be connected in a screw-coupling manner. When the coupler 510 press an outer side of the inserter 520, the rod 410 and the inserter 520 are coupled to the driving wheel 420 by the coupler 510. At this time, the driving wheel 420 and the inserter 520 rotate together, allowing the rod to move linearly in one direction.

The inserter 520 may have a predetermined flexibility so as to be engaged with the transmission module 400 by the elastic force applied by the coupler 510.

The coupler 510 is disposed on the outer side of the inserter 520, and when activated, may connect the rod 410 and the driving wheel 420. The coupler 510 is a component capable of pressing the outer side of the inserter 520 with an elastic force and is not limited to a specific shape. However, hereinafter, for convenience of description, a case in which the coupler has a spring shape will be mainly described.

The one end portion 511 of the coupler 510 may be detachably mounted on the driving wheel 420. The one end portion 511 is supported by the first supporter 424 and may be separated over the protrusion of the first supporter 424 by the pressing of the second flange 621. The other end portion of the coupler 510 is fixed to the driving wheel 420.

Accordingly, when the one end portion 511 of the coupler 510 is mounted on the driving wheel 420, the coupler 510 is mounted only on the driving wheel 420, and thus, the rod 410 and the driving wheel 420 are drivingly separated, but, when the one end portion 511 of the coupler 510 grips the inserter 520, the coupler 510 drivingly connects the rod 410 and the driving wheel 420.

When the clutch module 500 is not activated, the rod 410 and the inserter 520 may move in the inner space of the driving wheel 420 when a medical liquid is injected into the reservoir 200 for the storage of the medical liquid. Since a gap of g is formed between the inserter 520 and the coupler 510, when the coupler 510 does not grip the inserter 520, the rod 410 and the inserter 520 may move.

When the clutch module 500 is activated, the inserter 520 is also rotated when the driving wheel 420 rotates. At this time, since the rod 410 is coupled to the inserter 520, the rod 410 may linearly move forward by the rotation of the inserter 520.

The trigger module 600 may generate a mechanical signal that causes the medical liquid of the medical liquid infusion apparatus 1 to be injected. The trigger module 600 is pivotably disposed on one side of the base body 50, and the trigger module 600 may pivot to start driving of the driving module 300, and at the same time, the clutch module 500 may drivingly connect the transmission module 400 to the driving module 300.

The trigger module 600 may pivot in one direction around the pivot shaft 51. At this time, the trigger module 600 may press the clutch module 500 to couple the rod to the driving wheel 420. In addition, the trigger module 600 may release the contact with the starter 650 so that the starter 650 presses the driving shaft 330 to move a position of the contact member 350. The trigger module 600 may be partitioned into a plurality of bent portions.

The trigger module 600 may include the first end 610 extending to the needle assembly 100. The first end 610 may be disposed to be in contact with the first stopper 52, and when a user rotates the needle assembly 100, the knob 101 may press the first flange 611 to start pivoting of the trigger module 600, as shown in FIG. 3. After the first end 610 has pivoted, an incised groove 612 is supported by a sidewall 52b of the first stopper 52 to limit the pivoting of the trigger module 600 in an opposite direction.

The trigger module 600 may include the second end 620 extending to the clutch module 500. The second end 620 may extend from the first end 610 in a different direction, and may include the second flange 621 inserted between the one end portion 511 of the coupler 510 and the driving wheel 420. When the trigger module 600 rotates, the second flange 621 presses the one end portion 511 of the coupler 510, so that the coupler 510 is coupled to the inserter 520 to activate the clutch module 500.

The trigger module 600 may include a third end 630 extending to the driving module 300. The third end 630 extends toward the driving module 300 and may start driving of the driving module 300.

The third end 630 may include a support part 631 and a guide part 632, which are bent toward the driving shaft 330. Referring to FIGS. 6 and 8, the support part 631 may support the starter 650 before driving of the medical liquid infusion apparatus 1. The guide part 632 is disposed adjacent to the support part 631, and may support a sidewall of the moving terminal 340 or move along the sidewall.

The third end 630 maintains a fixed state of the driving shaft of the driving module 300 by the starter 650, but when the trigger module 600 pivots, the third end 630 is released from the contact with the starter 650, and the starter 650 presses the moving terminal 340 to start driving of the driving module 300.

As the trigger module 600 pivots, the starter 650 may move the driving module 300. When the contact with the trigger module 600 is released, the starter 650 may move the driving shaft 330 by pressing the moving terminal 340 of the driving module 300.

In an embodiment, the starter 650 may be formed in the form of a spring having a predetermined elastic force, but is not limited thereto, and may be formed in the form of a stick having a predetermined elasticity.

The starter 650 is disposed such that one end is mounted on the base body 50 and the other end supports an end portion of the trigger module 600. A pressing end 651 of the starter 650 is disposed between the moving terminal 340 and the support part 631 of the trigger module 600.

As the trigger module 600 pivots, the starter 650 may press the end portion of the driving shaft 330. The starter 650 remains in a compressed state before the medical liquid infusion apparatus 1, is driven, but when the contact with the support part 631 is released, the pressing end 651 presses the moving terminal 340 by an expansion force of the starter 650. At this time, the driving shaft 330 connected to the moving terminal 340 and the contact member 350 installed on the driving shaft 330 may be moved according to the movement of the moving terminal 340. Thereafter, an electrochemical reaction is started in the driving module 300, and driving of the driving module 300 is started.

The support part 631 of the trigger module 600 maintains the compressed state of the starter 650. The starter 650 is mounted on the base body 50 in a preset compressed state, but a compression force is not released since the support part 631 remains in a fixed position. The support part 631 of the trigger module 600 maintains contact with the pressing end 651 of the starter 650 to limit the movement of the starter 650.

The contact member 350 is located at a first position P1 on the inner surface of the cover 310, and a terminating end of the driving shaft 330 is located at a position of i. The first position P1 is defined as a position in which the contact member 350 is in contact with the inner surface of the cover 310 before the medical liquid infusion apparatus 1 is driven, and is not limited to a specific position. Since an external force is not transmitted to the driving shaft 330, the contact member 350 is located at the preset first position P1.

Here, since the clutch module 500 is not driven, the coupler 510 is not connected to the inserter 520. Accordingly, the rod of the transmission module 400 is drivingly separated from the driving wheel 420, and the medical liquid stored in the reservoir 200 is not introduced into the needle N.

The trigger module 600 rotates to release the contact between the support part 631 and the starter 650. When the knob 101 of the needle assembly 100 presses the first flange 611, the trigger module 600 pivots around the pivot shaft 51, and the support part 631 also pivots in a direction away from the moving terminal 340. At this time, the contact between the support part 631 and the pressing end 651 is released. At the same time, the pressing end 651 presses the moving terminal 340 to move the driving shaft 330. As the compression force is released, the pressing end 651 is brought into contact with the inclined surface 342a and moves along the inclined surface 342a. The pressing end 651 pushes the moving terminal 340 in the axial direction, and thus the moving terminal 340 and the driving shaft 330 move in a direction away from the driving module 300. The terminating end of the driving shaft 330 moves from the position of i to a position of j, and the contact member 350 moves together with the driving shaft 330 and is located at a second position P2. At this time, the clutch module 500 is driven so that the coupler 510 is coupled to the inserter 520. Since the one end portion 511 of the coupler 510 is separated from the driving wheel 420 and grips the outer side of the inserter 520, the driving wheel 420, the coupler 510, the inserter 520, and the rod are integrally driven.

The pressing end 651 may move over the inclined surface 342a. The pressing end 651 is located on the opposite side of the moving terminal 340 based on FIG. 8, and the contact with the moving terminal 340 is released. The moving terminal 340 may be supported on one side of the base body 50. At this time, an electrochemical reaction may be generated in the driving module 300, and a driving force for linearly reciprocating the driving shaft 330 may be generated. The result of the electrochemical reaction generated inside the driving module 300 causes changes in volumes of the first space S1 and the second space S2. These volume changes are transmitted to the driving shaft 330 by the driving force. That is, when the volume of the second space S2 increases, the driving shaft 330 moves forward, and when the volume of the second space S2 decreases, the driving shaft 330 moves backward. The movement of the driving shaft 330 linearly reciprocates the moving terminal 340, and the connection shaft 343 of the moving terminal 340 rotates the driving wheel 420 using the connector (not shown) to discharge the medical liquid from the reservoir 200.

Until the medical liquid infusion apparatus 1 is manufactured and then driven, the contact member 350 is in contact with a specific region (the first position P1) of the cover 310 for a long time. Since the contact member 350 includes a silicone-based or rubber-based material, the contact member 350 may be deformed due to the long-time contact and may be attached to the inner surface of the cover 310. When the contact member 350 is attached to an inner surface of the driving module 300, this may interfere with an initial driving of the driving module 300 and cause difficulty in discharging the medical liquid from the needle N in a quantitative amount.

The starter 650 moves the contact member 350 before the medical liquid infusion apparatus 1 is driven, so that the driving module 300 may have an optimized driving environment. In detail, when the contact between the starter 650 and the trigger module 600 is released, the starter 650 moves the driving shaft 330 of the driving module 300, so that the contact position of the contact member 350 may be changed before the driving module 300 is driven by an electrochemical reaction. Since the starter 650 moves the position of the contact member 350 from the first position P1 to the second position P2, the contact member 350 is removed from being attached and fixed to the inner surface of the driving module 300, and the initial driving of the driving module 300 may be smoothly performed.

The medical liquid infusion apparatus 1 according to an embodiment of the present disclosure may be simply and safely driven by a user. When the user rotates the sleeve 110 of the needle assembly 100, the cannula C in the needle assembly 100 is inserted into the subject, and the clutch module 500 connects the transmission module 400 to the driving module 300 to drive the driving module 300 so that the medical liquid is infused. Since driving of the driving module 300 is started simultaneously when the user rotates the sleeve 110, the medical liquid infusion apparatus 1 may be simply and safely used.

Since the driving module 300 is driven in an optimized driving environment, the medical liquid infusion apparatus 1 according to an embodiment of the present disclosure may quantitatively discharge the medical liquid. The starter 650 moves the position of the driving shaft 330 before the driving module 300 is driven, thereby preventing the contact member 350 from being attached to the inner surface of the driving module 300 and interfering with the driving of the driving module 300. By improving the storability and maintaining the precision of the medical liquid infusion apparatus 1, even when the medical liquid infusion apparatus 1 is driven after being stored for a long time, the driving module 300 may be driven smoothly and may quantitatively discharge the medical liquid to the subject.

The medical liquid infusion apparatus 1 according to an embodiment of the present disclosure may safely and quantitatively infuse a medical liquid into a subject since the structures for discharging the medical liquid are drivingly connected by the clutch module 500 after the cannula C of the needle assembly 100 is inserted into the subject.

The medical liquid infusion apparatus 1 according to an embodiment of the present disclosure is intuitively driven by the rotation of the needle assembly 100, rotation directions of the needle assembly 100 and the trigger module 600 are limited in one direction, and a rotation distance is limited to a preset distance, thereby securing user safety.

Figure 9:
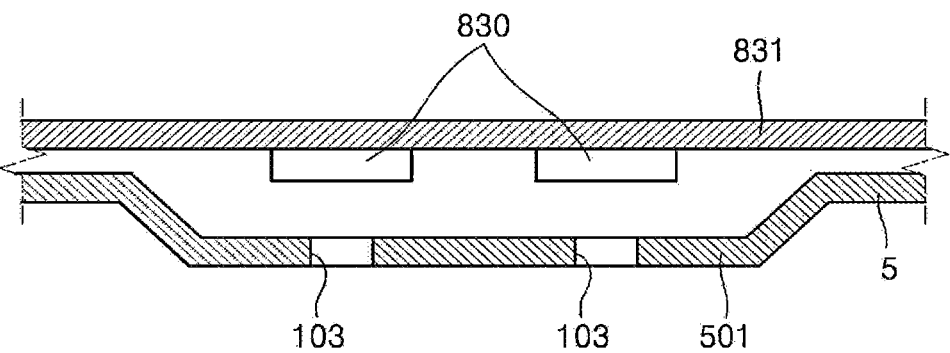
FIGS. 9 and 10 are views illustrating a cross section of a portion of an activator installed adjacent to an entry hole of a housing.
Figure 10:
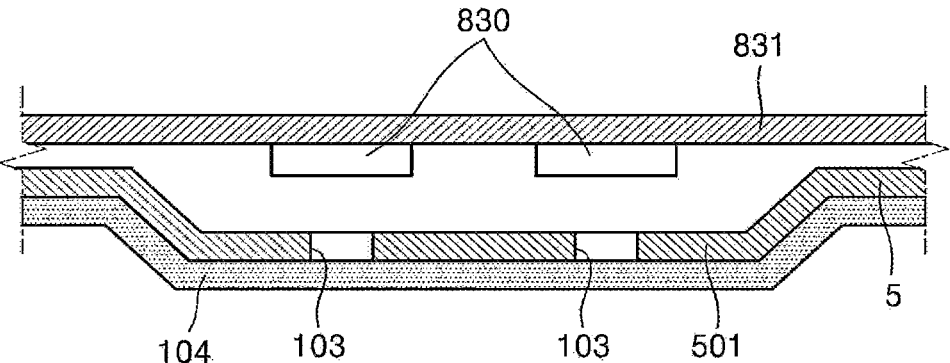

FIGS. 9 and 10 are views illustrating a cross section of a portion of the activator 830 installed adjacent to the entry hole 103 of the housing 5.

The activator 830 may be formed on a substrate 831 accommodated in the housing 5. The activator 830 is formed to be aligned with the entry hole 103 on a surface of the substrate 831 corresponding to the entry hole 103. The activator 830 may be electrically connected to the control module 800 and/or another electronic module by wiring patterns (not shown) formed on the substrate 831. According to an embodiment, the activator 830 may be formed of a conductive material on the substrate 831. By allowing the housing 5 to be spaced further apart from the substrate 831 in a region where the activator 830 is formed, the activator 830 may not interfere with the housing 5.

The activator 830 may include a plurality of electrode pads separated from each other. According to an embodiment, one of the electrode pads may be a first electrode pad configured to be electrically connected to an external power supply line. The first electrode pad may be electrically connected to the battery module 700 and/or the control module 800. According to another embodiment, one of the electrode pads may be a second electrode pad including an Rx terminal and/or a Tx terminal for providing a physical interface between the driving module 300 and external wired communication devices (including a universal asynchronous receiver/transmitter (UART), a Serial Peripheral Interface (SPI), Inter-Integrated Circuit (I2C), In system programming (ISP), In-circuit serial programming (ICSP), and the like) The second electrode pad may be electrically connected to the driving module 300 and/or the control module 800. According to another embodiment, one of the electrode pads may be a third electrode pad including a switching power-on terminal for enabling the driving module 300 to be booted by an external device. The third electrode pad may be electrically connected to the driving module 300. According to another embodiment, one of the electrode pads may also include a terminal configured to test various electronic modules accommodated in the housing.

The activator 830 may be configured to be electrically connected to another external electronic device through the entry hole 103 at a first time point. The first time point may be any one time point, such as immediately after the manufacturing process and/or assembly of the medical liquid infusion apparatus 1 is completed. Optionally, in this state, the other electronic devices in the housing 5 may be in a state of being electrically disconnected from the battery module 700 by the switching unit 803.

At this first time point, various tests and the like may be required in some cases. For these tests, no other electronic devices can be connected to the battery module 700. In the case of the medical liquid infusion apparatus 1, which may be delivered to a consumer in a state in which the battery module 700 is embedded therein, it is preferred that the medical liquid infusion apparatus 1 remains asleep until operated by a user to initiate use since battery drain from the battery module 700 between deliveries to the customer should be minimized. This is even more necessary when the medical liquid infusion apparatus 1 is used as a disposable module.

However, various electronic modules of the medical liquid infusion apparatus 1 must undergo many tests in a manufacturing process, and it is not always possible to wake up all the devices and maintain connections with the battery module 700.

According to embodiments of the present disclosure, by allowing various electronic modules in the medical liquid infusion apparatus 1 to be electrically connected to the external electronic equipment through the activator 830, the various electronic modules of the medical liquid infusion apparatus 1 may be tested without waking up the entire apparatus or directly using power of the battery module 700, which allows the apparatus to be manufactured reliably without consuming the battery.

When these tests are finally completed, the inside of the medical liquid infusion apparatus 1 may be sanitary treated through the entry hole 103. The sanitary treatment may be accomplished by injecting a sanitary gas into the medical liquid infusion apparatus 1 through the entry hole 103. The sanitizing gas may be a sterilizing gas, a germicidal gas, a disinfecting gas, or the like that is capable of killing germs or microorganisms.

When the sanitary treatment is completed, the cover body 104 is attached to an outer side of the housing 5 to cover the entry hole 103. The cover body 104 may be in the form of a film as described above, but the present disclosure is not necessarily limited thereto, and the cover body 104 may also be in the form of a rigid plate. After sealing is performed once, the housing is not opened to mount the battery module, so that the sanitary condition of the entire system of the medical liquid infusion apparatus 1 may be maintained.

In addition, in a state in which the sanitary treatment is completed, the entire system of the medical liquid infusion apparatus 1 remains in a sleep state, thereby minimizing battery consumption in a distribution process.

Hereinafter, a medical liquid infusion apparatus 1010 according to another embodiment of the present disclosure will be described.

Figure 11:
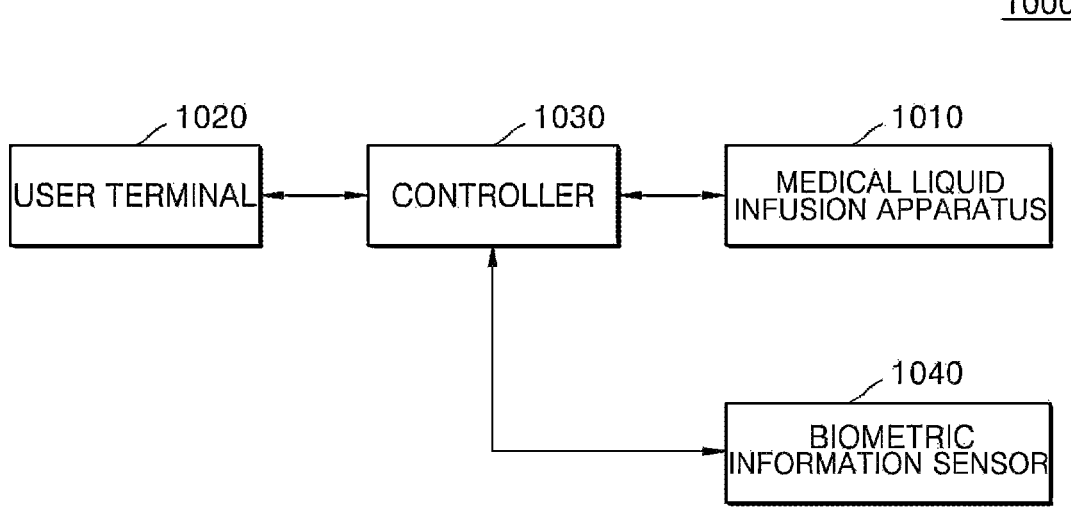
FIG. 11 is a block diagram illustrating a medical liquid infusion system according to an embodiment of the present disclosure.

FIG. 11 is a block diagram illustrating a medical liquid infusion system 1000 according to an embodiment of the present disclosure.

Referring to FIG. 11, the medical liquid infusion system 1000 may include the medical liquid infusion apparatus 1010, a user terminal 1020, a controller 1030, and a biometric information sensor 1040. A user may drive and control the medical liquid infusion system 1000 by using the user terminal 1020, and periodically infuse a medical liquid from the medical liquid infusion apparatus 1010 on the basis of blood sugar information monitored by the biometric information sensor 1040.

The medical liquid infusion apparatus 1010 performs a function of infusing a medical liquid such as insulin, gluca- gon, anesthetic, pain killer, dopamine, growth hormone, non-smoking aids, or the like to be infused to the user on the basis of data sensed by the biometric information sensor 1040.

In addition, the medical liquid infusion apparatus 1010 may transmit a device state message including information on a remaining battery capacity of the device, whether the device is booted successfully, whether the infusion is suc- cessful, or the like to the controller 1030. Messages trans- mitted to the controller 1030 may be transmitted to the user terminal 1020 via the controller. Alternatively, the controller 1030 may transmit improved data obtained by processing the received messages to the user terminal 1020.

In an embodiment, the medical liquid infusion apparatus 1010 may be provided separately from the biometric infor- mation sensor 1040 and installed to be spaced apart from an object. In another embodiment, the medical liquid infusion apparatus 1010 and the biometric information sensor 1040 may be provided as one device.

In an embodiment, the medical liquid infusion apparatus 1010 may be mounted on a user's body. In addition, in another embodiment, the medical liquid infusion apparatus 1010 may also be mounted on an animal and may infuse a medical liquid thereto.

The user terminal 1020 may receive an input signal from the user in order to drive and control the medical liquid infusion system 1000.

The user terminal 1020 may drive the medical liquid infusion apparatus 1010 by generating a signal for driving the controller 1030 and controlling the controller 1030.

In addition, the user terminal 1020 may display biometric information measured from the biometric information sen- sor 1040, and may display information on a state of the medical liquid infusion apparatus 1010.

The user terminal 1020 refers to a communication termi- nal that can be used in a wired/wireless communication environment. For example, the user terminal 1020 may be a smartphone, a tablet personal computer (PC), a PC, a smart television (TV), a mobile phone, a personal digital assistant (PDA), a laptop computer, a media player, a micro-server, a global positioning system (GPS) device, an electronic book terminal, a digital broadcasting terminal, a navigation device, a kiosk, an MP3 player, a digital camera, a home appliance, a device equipped with a camera, or another mobile or non-mobile computing device.

In addition, the user terminal 1020 may be a wearable device, such as a watch, glasses, a hairband, or a ring, having a communication function and a data processing function However, a terminal equipped with an application capable of Internet communication as described above may be unlim- itedly employed.

The user terminal 1020 may be connected to a pre- registered controller 1030 on a one-to-one basis. The user terminal 1020 may establish an encryption connection with the controller 1030 in order to prevent the controller 1030 from being driven and controlled from an external device.

In an embodiment, the user terminal 1020 and the con- troller 1030 may be separately provided as separate devices. For example, the controller 1030 may be provided to a target person having the medical liquid infusion apparatus 1010 mounted thereon, and the user terminal 1020 may be pro- vided to the target person or a third person. The user terminal 1020 may be driven by a guardian so that the safety of the medical liquid infusion system 1000 may be improved.

In another embodiment, the user terminal 1020 and the controller 1030 may be provided as one device. The con- troller 1030 provided together with the user terminal 1020 as one device may communicate with the medical liquid infu- sion apparatus 1010 and control infusion of a medical liquid.

The controller 1030 performs a function of transmitting and receiving data to and from the medical liquid infusion apparatus 1010, and may transmit a control signal related to infusion of a medical liquid such as insulin to the medical liquid infusion apparatus 1010, and receive a control signal related to a measurement of a biometric value such as a blood sugar level from the biometric information sensor 1040.

In an example, the controller 1030 may transmit an instruction request for measuring a current state of a user to the medical liquid infusion apparatus 1010, and receive measurement data from the medical liquid infusion appara- tus 1010 in response to the instruction request.

The biometric information sensor 1040 may perform a function of measuring a biometric value such as a blood sugar value, blood pressure, or a heart rate of a user according to the purpose. Data measured by the biometric information sensor 1040 may be transmitted to the controller 1030, and a period and/or infusion amount of the medical liquid may be set on the basis of the measured data. The data measured by the biometric information sensor 1040 may be transmitted to the user terminal 1020 and displayed.

In an example, the biometric information sensor 1040 may be a sensor configured to measure a blood sugar level of the subject. The biometric information sensor 1040 may be a continuous glucose monitor (CGM) sensor. The GSM sensor may be attached to the subject and may continuously monitor a blood sugar level.

The user terminal 1020, the controller 1030, and the medical liquid infusion apparatus 1010 may perform communication by using a network.

For example, the network may include a local area network (LAN), a wide area network (WAN), a value-added network (VAN), a mobile radio communication network, a satellite communication network, or a combination thereof. The network is a data communication network in a comprehensive sense that enables network components to communicate with each other smoothly, and may include a wired Internet, a wireless Internet, or a mobile wireless communication network.

In addition, wireless communication may include, for example, wireless LAN (Wi-Fi), Bluetooth, Bluetooth low energy (BLE), Zigbee, Wi-Fi direct (WFD), ultra-wideband (UWB), infrared data association (IrDA), near field communication (NFC), 5th-Generation (5G), or the like, but the present disclosure is not limited thereto.

Figure 12:
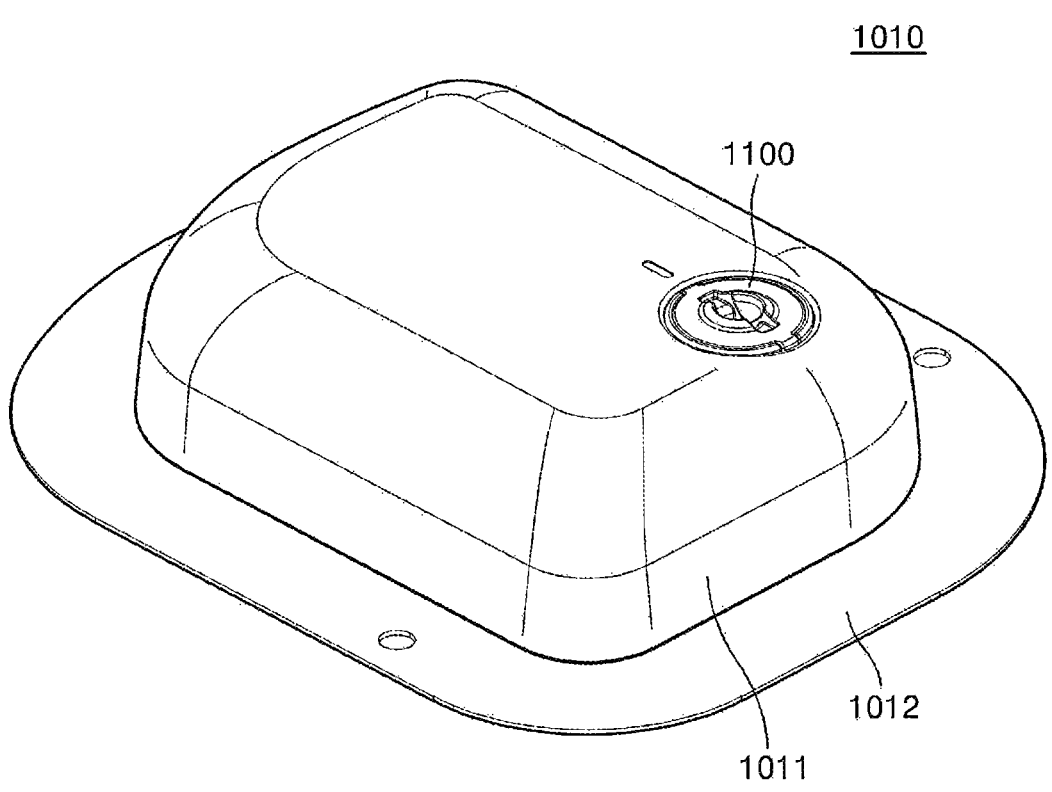
FIG. 12 is a perspective view illustrating a medical liquid infusion apparatus according to an embodiment of the present disclosure.
Figure 13:
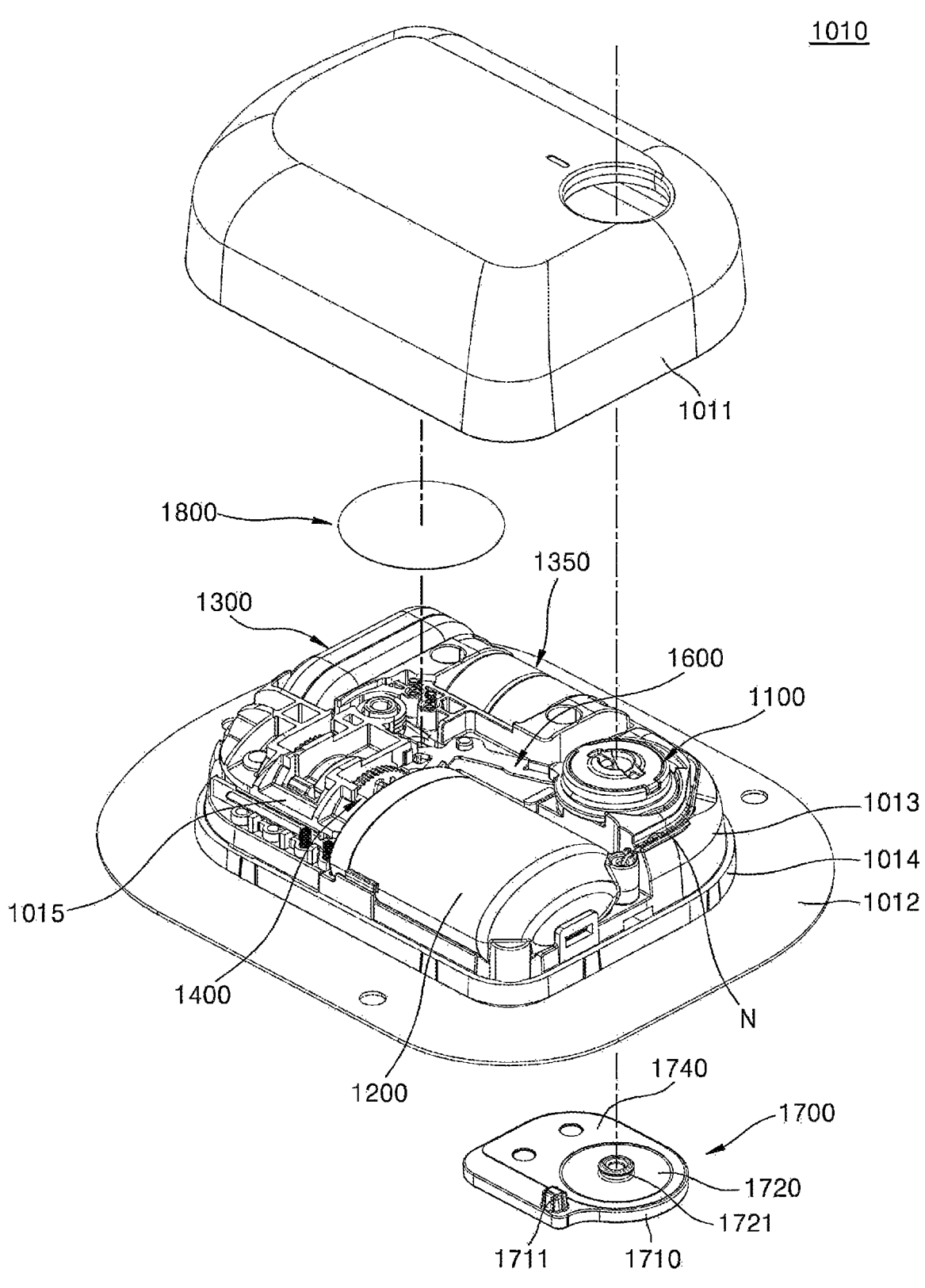
FIG. 13 is an exploded perspective view of the medical liquid infusion apparatus of FIG. 12.
Figure 14:
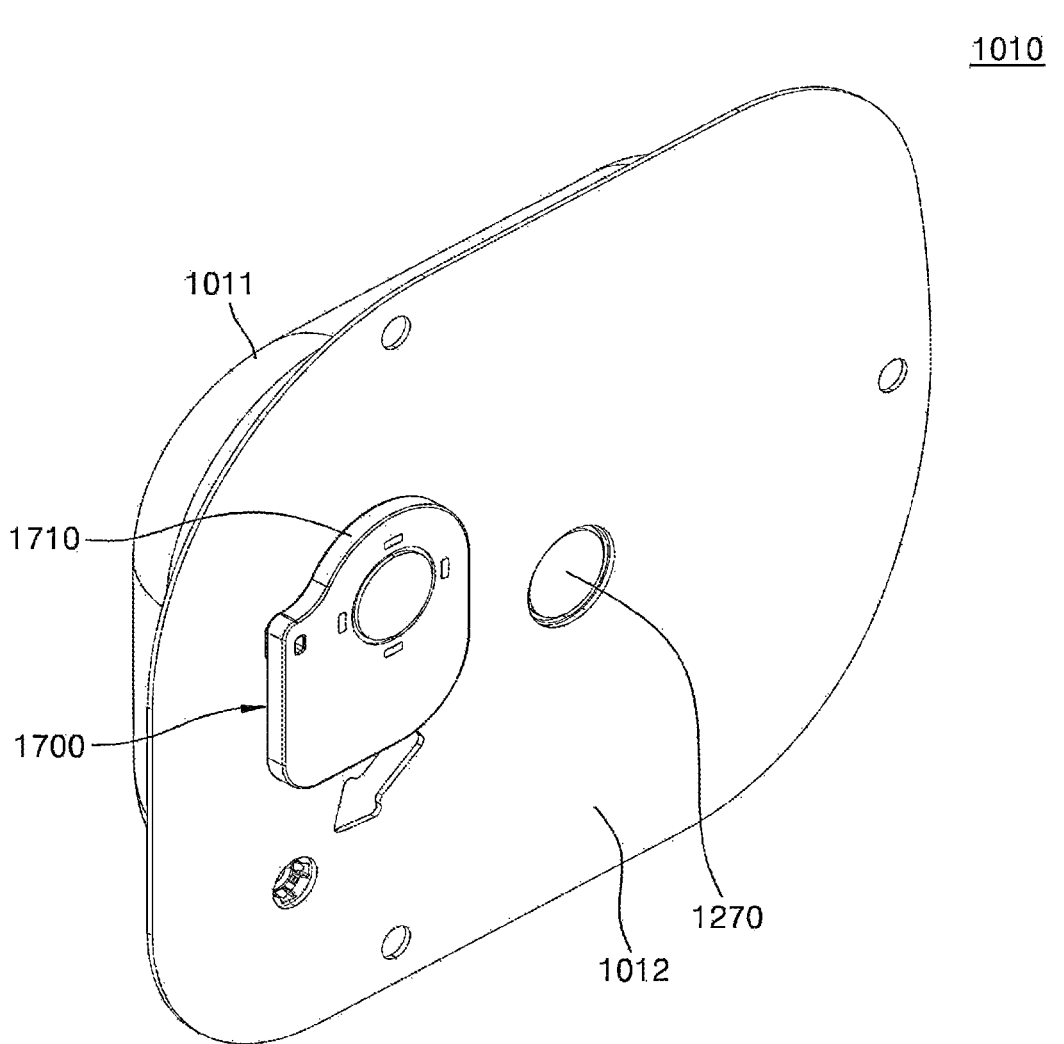
FIG. 14 is a bottom perspective view illustrating the medical liquid infusion apparatus according to an embodiment of the present disclosure.

FIG. 12 is a perspective view illustrating the medical liquid infusion apparatus 1010 according to an embodiment of the present disclosure, FIG. 13 is an exploded perspective view of the medical liquid infusion apparatus 1010 of FIG. 12, and FIG. 14 is a bottom perspective view illustrating the medical liquid infusion apparatus according to an embodiment of the present disclosure.

Referring to FIGS. 12 to 14, the medical liquid infusion apparatus 1010 may be attached to a user into which a medical liquid is infused, and may quantitatively infuse a medical liquid stored therein to the user.

The medical liquid infusion apparatus 1010 may be used for various purposes depending on the type of medical liquid to be infused. For example, the medical liquid may include an insulin-based medical liquid for a diabetic patient, and may include a medical liquid for other pancreas, a medical liquid for heart, and other various types of medical liquids.

Referring to FIGS. 12 to 14, the medical liquid infusion apparatus 1010 according to an embodiment of the present disclosure may include a housing 1011 that forms an outer appearance and covers an outer side, and an attachment portion 1012 located adjacent to a user's skin.

The medical liquid infusion apparatus 1010 includes a plurality of components disposed in an inner space between the housing 1011 and the attachment portion 1012. A separate bonding means may be further interposed between the attachment portion 1012 and the user's skin, and the medical liquid infusion apparatus 1010 may be fixed to the skin by the bonding means.

The medical liquid infusion apparatus 1010 may include a needle assembly 1100, a reservoir unit 1200, a driving module 1300, a battery 1350, a driving unit 1400, a clutch unit 1500, a trigger member 1600, a needle cover assembly 1700, an alarm unit 1800, and a plurality of sensor units.

Referring to FIG. 12, in the medical liquid infusion apparatus 1010, a base body may form a frame in which the at least one body supports the internal components. The base body may include a first body 1013, a second body 1014, a third body 1015, and a lower cover 1017 according to the arrangement.

The first body 1013 is disposed below the housing 1011, and the needle assembly 1100, the reservoir unit 1200, the driving module 1300, the battery 1350, and the like may be supported in respective openings or grooves.

The second body 1014 is disposed below the first body 1013, and may be connected to the attachment portion 1012.

The second body 1014 may cover a lower portion of the medical liquid infusion apparatus 1010.

The third body 1015 is disposed above the first body 1013, and the reservoir unit 1200, the driving module 1300, the battery 1350, the driving unit 1400, and the like may be supported in respective openings or grooves. The first body 1013, the second body 1014, and the third body 1015 are illustrated in the drawings, but are not limited thereto, and may be provided as a single body or a plurality of bodies.

Figure 15:
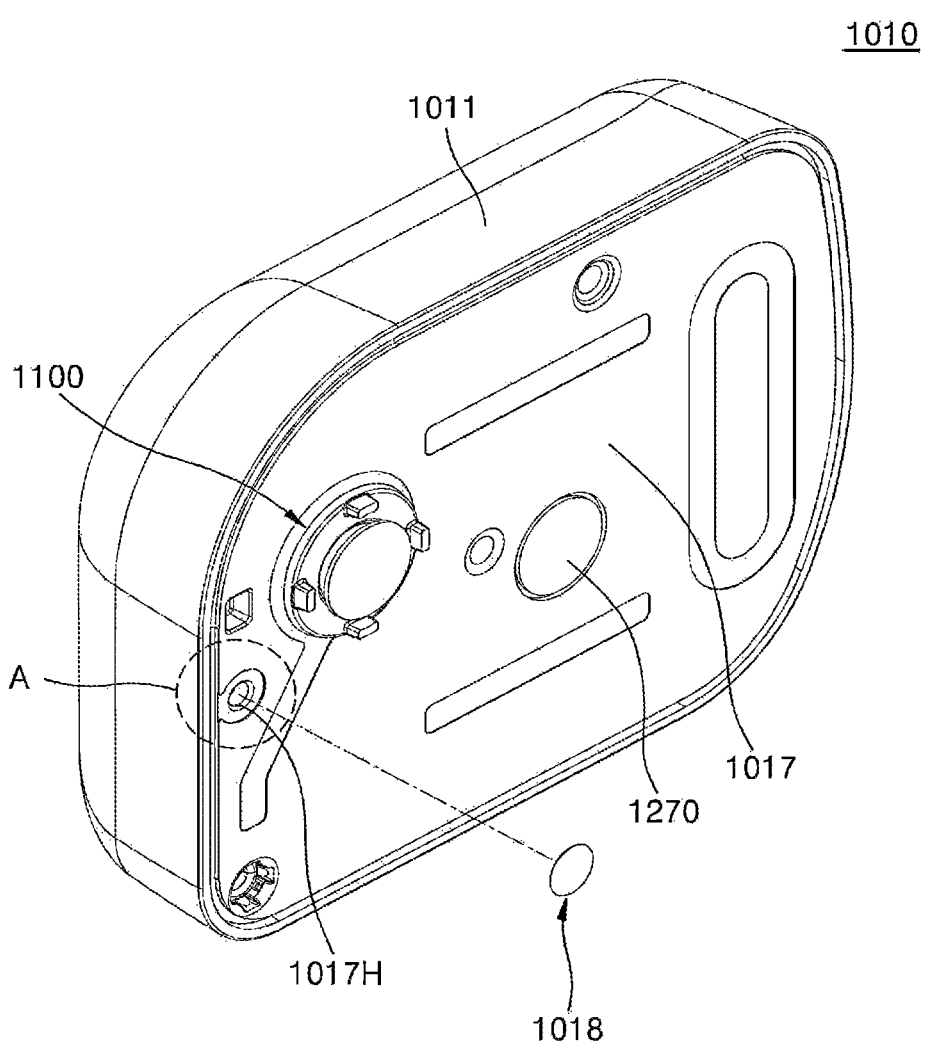
FIG. 15 is a view illustrating a state in which an attachment portion is removed in FIG. 14.
Figure 19A:
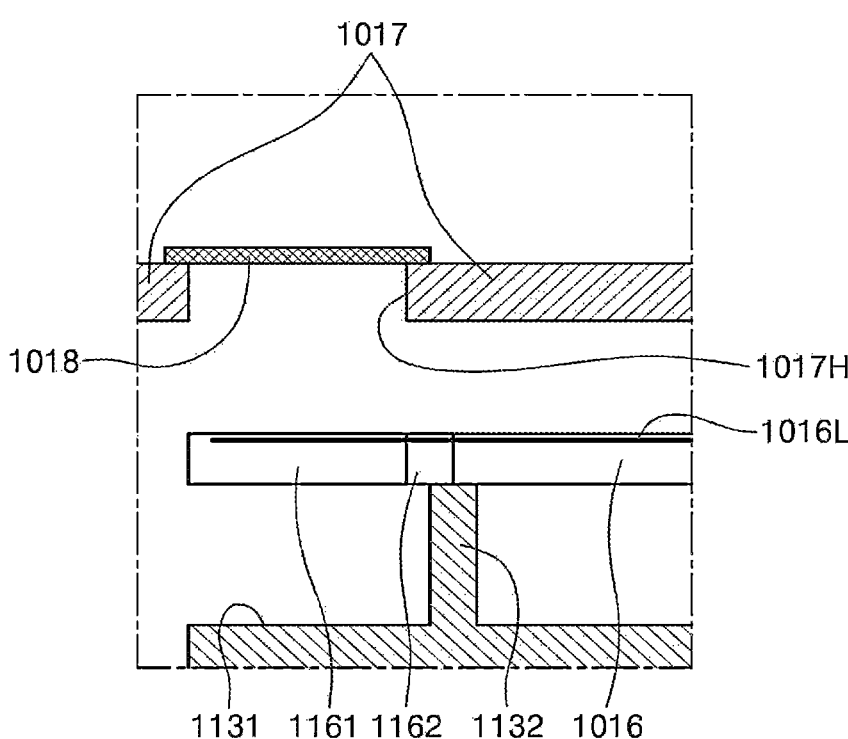
FIGS. 19A and 19B are partially enlarged side cross-sectional views of portion A of FIG. 15.
Figure 19B:
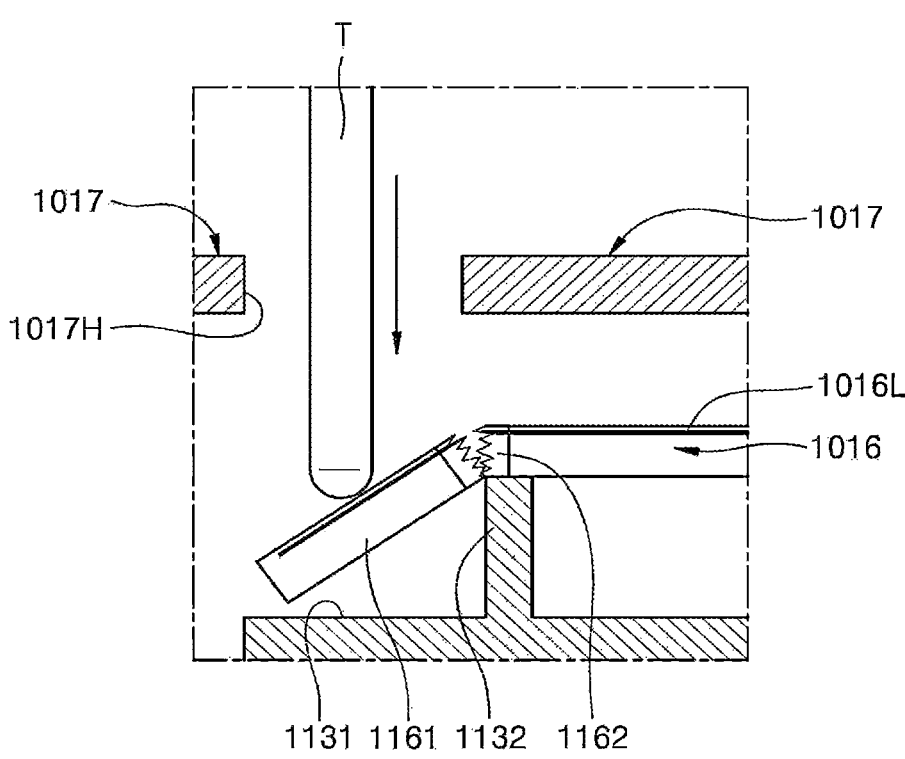

Referring to FIGS. 15, 19A, and 19B, the lower cover 1017 according to an embodiment of the present disclosure is disposed to face the attachment portion 1012 and may be disposed on an inner side of the housing 1011.

Specifically, the lower cover 1017 covers an opening (its reference numeral is not assigned) formed on one side (a lower side based on FIG. 13) of the housing 1011, and may be connected to the first body 1013 on which the needle assembly 1100, the reservoir unit 1200, the driving module 1300, the battery 1350, and the like are supported.

In other words, the lower cover 1017 may be disposed between the first body 1013 and the attachment portion 1012. The lower cover 1017 may have an opening or a groove formed to support the needle assembly 1100, and may be connected to the first body 1013 so as to be positionally fixed thereto while covering the driving module 1300, the battery 1350, and the like disposed over an opening formed in the first body 1013.

The lower cover 1017 according to an embodiment of the present disclosure may be formed in a flat plate shape, and a pass-through hole 1017H may be formed therein to correspond to a position of a fracture portion 1161 formed in a control module 1016 to be described below.

Referring to FIGS. 16, 17, 19A, 19B, and 20, the control module 1016 may be disposed inside the medical liquid infusion apparatus 1010.

The control module 1016, which is a circuit board, is disposed below the second body 1014, and specifically, may be disposed between the lower cover 1017 and the first body 1013 in an inside of the housing 1011. The control module 1016 may be covered by the lower cover 1017.

Figure 20:
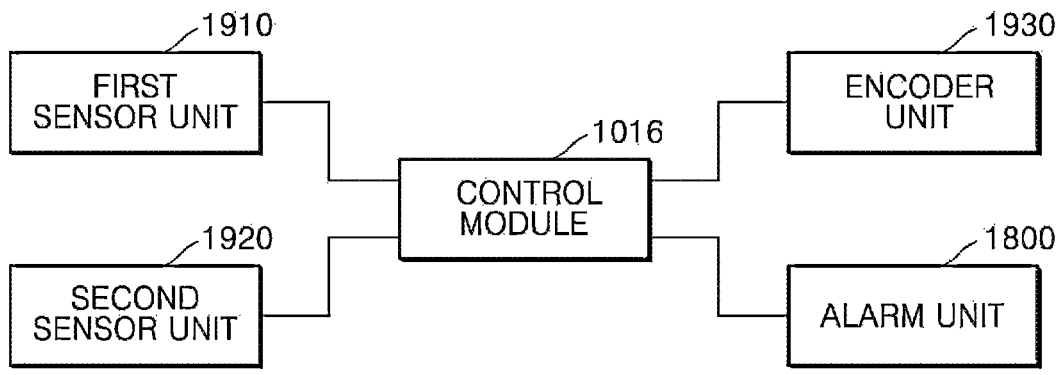
FIG. 20 is a block diagram illustrating some components of the medical liquid infusion apparatus of FIG. 12.

Referring to FIG. 20, the control module 1016 according to an embodiment of the present disclosure may control overall driving of the medical liquid infusion apparatus 1010. The control module 1016 is in electrical contact and connection with the internal devices such as the driving module 1300, the battery 1350, the alarm unit 1800, and the plurality of sensor units, and may control driving thereof.

Referring to FIGS. 16, 17, 19A, and 19B, the fracture portion 1161 may be formed to protrude outward from one side of the control module 1016 according to an embodiment of the present disclosure.

A control line 1016L, which is an electrical connection of the alarm unit 1800 and the control module 1016, specifically, a movement path of an alarm signal, may be located on the fracture portion 1161. As an external force due to a tool T such as a rod is applied to the fracture portion 1161, and the control line 1016L is fractured by the external force, the control module 1016 may be electrically disconnected from the electrically connected internal devices.

As described above, the term "internal devices" as used herein refers to components that are installed inside the medical liquid infusion apparatus 1010 and driven by receiving power, such as the driving module 1300, the battery 1350, the alarm unit 1800, and the plurality of sensor units.

Referring to FIGS. 19A and 19B, the control line 1016L may be disposed on an upper side (based on FIG. 19A) of the fracture portion 1161. Specifically, the control line 1016L may be disposed close to one surface (an upper surface based on FIG. 19A) of the fracture portion 1161, which faces the pass-through hole 1017H, with respect to a center portion of the fracture portion 1161 in a height direction.

Accordingly, when a user applies an external force to the fracture portion 1161 by using the tool T or the like, the control line 1016L disposed close to the surface of the fracture portion 1161 is broken first even when the fracture portion 1161, with which the tool T is brought into contact, is not completely cut, and the electrical connection between the alarm unit 1800 and the control module 1016 may be disconnected.

However, the present disclosure is not limited thereto, and the control line 1016L may be formed as a movement path of an alarm signal as well as a movement path of driving signals for the internal devices such as the plurality of sensor units, and various modified embodiments are possible, such as allowing a user to release the driving of the internal device by breaking the control line 1016L located on the fracture portion 1161.

Referring to FIGS. 16, 17, 19A, and 19B, in the fracture portion 1161 formed in the control module 1016 according to an embodiment of the present disclosure, a boundary may be formed, in which a notch 1162 may be formed in the shape of a groove.

Specifically, the notch 1162 may be formed at a boundary between a region in which the fracture portion 1161 is formed to protrude and a region in which the fracture portion 1161 is not formed, in the control module 1016. A plurality of notches 1162 may be provided, and may be formed on opposite sides with respect to a central axis of the fracture portion 1161 in the longitudinal direction.

Figure 17:
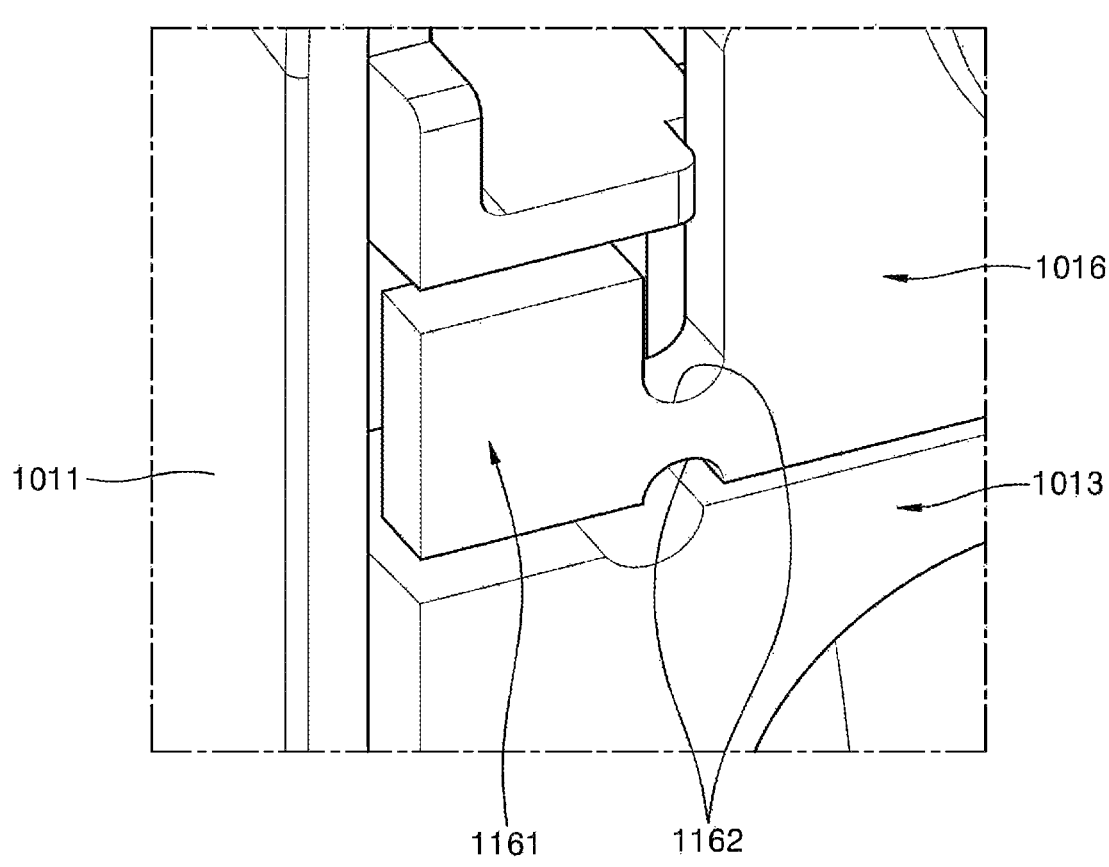
FIGS. 17 and 18 are enlarged views of portion B of FIG. 16.

Referring to FIG. 17, on the fracture portion 1161 protruding outward from the control module 1016 according to an embodiment of the present disclosure, the region in which the notch 1162 is formed may be formed with a relatively narrow width as compared to the region in which the notch 1162 is not formed.

Figure 16:
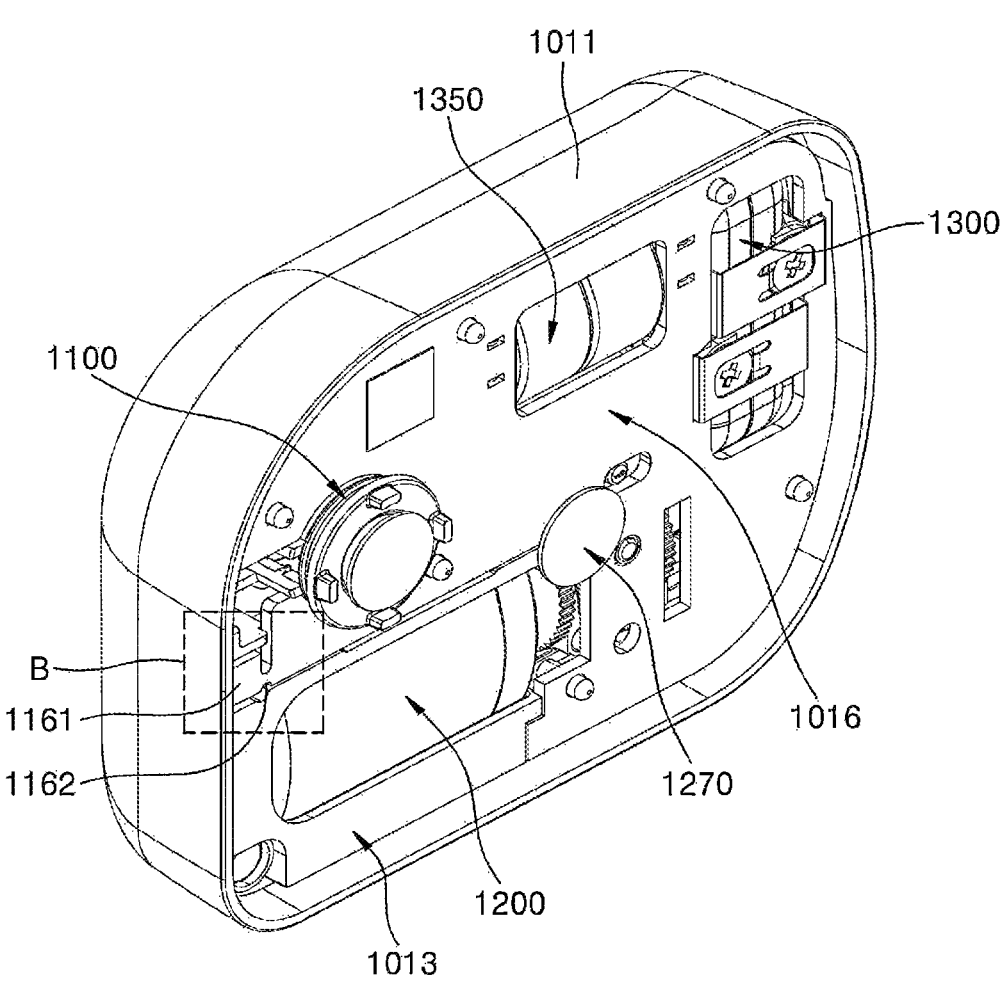
FIG. 16 is a view illustrating a state in which a lower cover is removed in FIG. 15.

Accordingly, when an external force is applied to the region on the fracture portion 1161, in which the notch 1162 is not formed, stress is concentrated in the region in which the notch 1162 is formed, which is a relatively narrowly formed region, and when an external force exceeding a threshold value is applied, the fracture portion 1161, specifically the region in which the notch 1162 is formed, may be fractured as shown in FIG. 19B. As the region in which the notch 1162 is formed is fractured, the control line 1016L formed across the control module 1016, specifically the fracture portion 1161 and the notch 1162, may be broken, and the control module 1016 may be electrically disconnected from the electrically connected alarm unit 1800. Referring to FIGS. 16 and 17, the notch 1162 according to an embodiment of the present disclosure may be formed to be rounded in a curved shape.

However, the notch 1162 is not limited thereto, and various modified embodiments are possible, such as forming the notch 1162 in a "V" shape, within the technical idea of forming a relatively narrow width at a predetermined section along the fracture portion 1161.

Although not shown in the drawings, a thickness of the fracture portion 1161 in the region in which the notch 1162 is formed may be formed to be relatively thinner than that in the region in which the notch 1162 is not formed.

Accordingly, by allowing stress to be concentrated in the region in which the notch 1162 is formed, when an external force caused by the tool T is applied to the fracture portion 1161, the fracture portion 1161 may be easily fractured as the fracture portion 1161 is folded.

Figure 18:
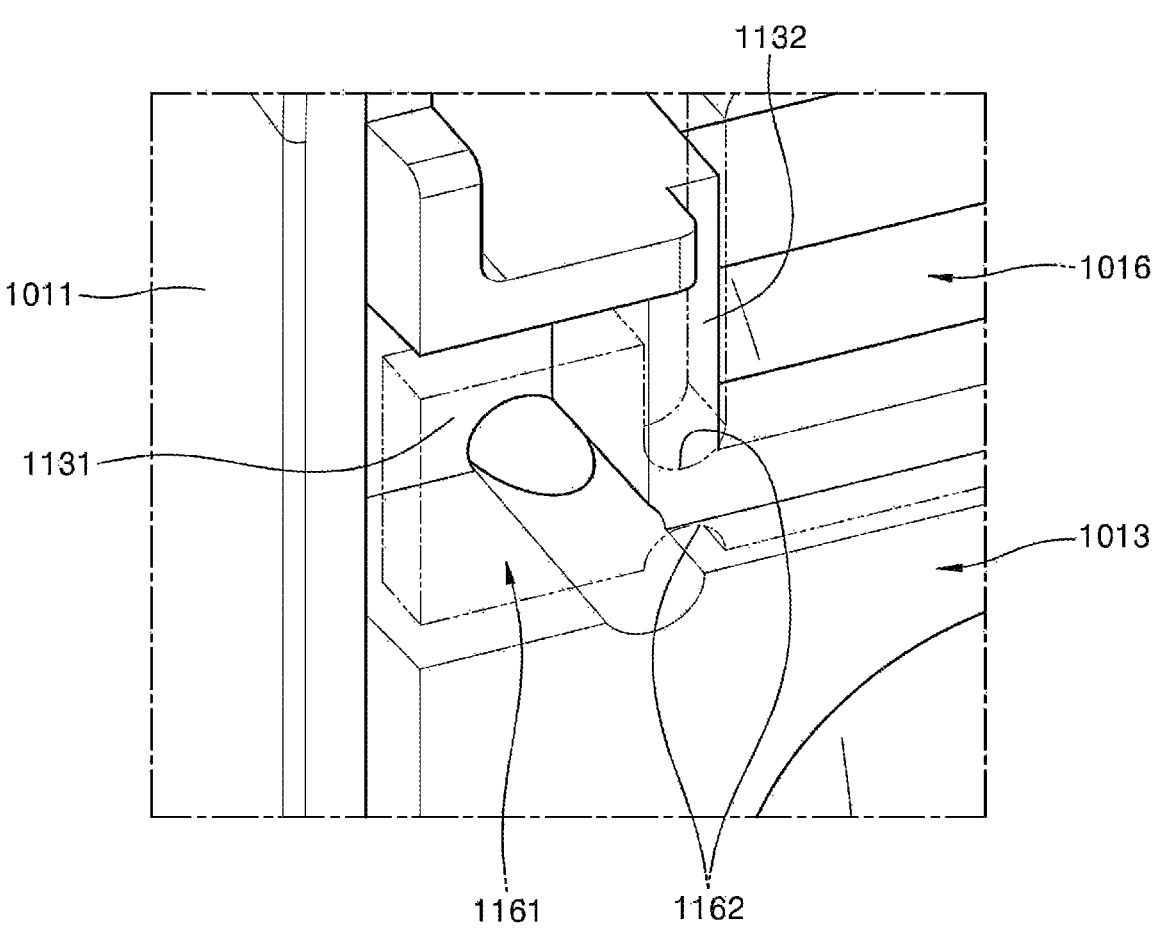

Referring to FIGS. 17 and 18, in the first body 1013 according to an embodiment of the present disclosure, an accommodation portion 1131 and a support portion 1132 may be formed in a region facing the fracture portion 1161.

Referring to FIGS. 17, 18, 19A, and 19B, the accommodation portion 1131 is formed in the shape of a groove, and a bottom portion (its reference numeral is not assigned) of the accommodation portion 1131 may be formed to be spaced apart from the control module 1016, specifically, the fracture portion 1161, by a predetermined distance.

Accordingly, when an external force is applied to the fracture portion 1161, and the fracture portion 1161 is fractured, a space in which the fracture portion 1161 may be folded until the fracture portion 1161 is fractured may be secured, and even after the fracture portion 1161 is fractured, the fracture portion 1161 may be accommodated in the accommodation portion 1131 formed in the first body 1013, and the component fractured in the control module 1016 may be prevented from moving around inside the housing 1011.

Referring to FIGS. 18, 19A, and 19B, the support portion 1132 may be formed to protrude from one surface of the first body 1013 according to an embodiment of the present disclosure, specifically, one surface of the accommodation portion 1131, toward a predetermined region of the fracture portion 1161, specifically, the region in which the notch 1162 is formed.

The support portion 1132 may be in contact with the region in which the notch 1162 is formed on the fracture portion 1161 as an external force is applied to the fracture portion 1161, and as the support portion 1132 is in contact with and supports the region in which the notch 1162 is formed, the fracture portion 1161 may be easily fractured by the external force applied by the tool T.

Specifically, referring to FIGS. 19A and 19B, when a user applies an external force to the fracture portion 1161 in a downward direction (based on FIG. 19B) from an upper side by using the tool T, the support portion 1132 supports the fracture portion 1161 in a direction opposite to a direction in which the external force acts (in a upward direction from a lower side based on FIG. 19B), so that the fracture portion 1161 may be easily fractured by the external force.

Referring to FIGS. 15 and 16, the control module 1016 in which the fracture portion 1161 is formed to protrude may be covered by the lower cover 1017, and the pass-through hole 1017H may be formed in the lower cover 1017 at a position corresponding to a position of the control module 1016, specifically, the fracture portion 1161.

Referring to FIG. 15, a fracture cover 1018 may be attached to the pass-through hole 1017H formed in the lower cover 1017.

The pass-through hole 1017H may be maintained, by the fracture cover 1018, in a closed state during normal operation.

Referring to FIGS. 15, 19A, and 19B, the fracture cover 1018 is disposed to face the fracture portion 1161, and may open and close a path through which an external force is applied to the fracture portion 1161.

Meanwhile, when an error occurs in the operation of the alarm unit 1800 due to an unexpected situation after the medical liquid infusion apparatus 1010, specifically, the attachment portion 1012, is attached to a user, a situation may occur in which an unnecessary alarm is transmitted to the user.

Referring to FIGS. 19A and 19B, the user may remove the fracture cover 1018 covering the pass-through hole 1017H from the lower cover 1017, pass the tool T such as a rod through the pass-through hole 1017H, and bring the tool T into contact with the control module 1016, specifically, the fracture portion 1161.

According to an embodiment of the present disclosure, the fracture cover 1018 may be formed of a thin film, and various modified embodiments are possible, such as using the tool T, such as a rod, to break the fracture cover 1018, e.g., by tearing the fracture cover 1018, and bring the tool T into contact with the control module 1016 disposed on a lower side of the fracture cover 1018, specifically, the fracture portion 1161, even in a state where the fracture cover 1018 is attached to the lower cover 1017 without being removed from the lower cover 1017 by the user.

Referring to FIG. 19B, in the state in which the tool T is in contact with the fracture portion 1161, the user may further apply a force in one direction (downward direction based on FIG. 19B), causing a fracture to occur in the region of the notch 1162, which is formed with a relatively narrow width, on the fracture portion 1161. The fracture of the fracture portion 1161 may cause the control line 1016L, which is located at the fracture portion 1161 where the notch 1162 is formed, to fracture, and the electrical connection between the control module 1016 and the alarm unit 1800 may be disconnected.

As the electrical connection between the control module 1016 and the alarm unit 1800 is disconnected, an unnecessary alarm, which continues to occur due to the malfunction of the alarm unit 1800 after the medical liquid infusion apparatus 1010 is attached to the user, may be prevented.

However, the present disclosure is not limited thereto, and the control line 1016L may be formed as a movement path of an alarm signal as well as a movement path of driving signals for the internal devices such as the plurality of sensor units, and various modified embodiments are possible, such as allowing a user to release driving of the internal device by breaking the control line 1016L located on the fracture portion 1161.

Although not shown in the drawings, in another embodiment of the present disclosure, a hole may be formed in the fracture portion 1161, and the hole shares a center with the pass-through hole 1017H formed in the lower cover 1017, Due to the hole formed in the fracture portion 1161, the tool T such as a rod passes through the pass-through hole 1017H formed in the lower cover 1017 to be hung in the hole formed in the fracture portion 1161, and stress is concentrated in the region in which the notch 1162 is formed while guiding the direction of the external force applied to the fracture portion 1161, so that the fracture portion 1161 may be easily fractured.

The needle assembly 1100 may be mounted on the first body 1013. In the needle assembly 1100, a needle N and/or a cannula may be moved in the axial direction as a sleeve 1110 rotates.

One end of the needle N may be connected to the reservoir unit 1200 so that a medical liquid may be transmitted therethrough, and the other end thereof may be inserted into the cannula and may move along the cannula.

The cannula has a tube shape capable of receiving the needle N, so that the medical liquid discharged from the needle N may be infused into the user.

The cannula maintains a state of being inserted into the user's skin, but the needle N is lifted and separated from the subject. However, the cannula and the needle N form a path through which a fluid moves, so that a medical liquid injected from a reservoir 1210 may be infused to the user through the needle N and the cannula.

The medical liquid infusion apparatus 1010 may insert the cannula into the subject and start a medical liquid infusion as the user simply rotates the needle assembly 1100.

The reservoir unit 1200 is mounted on the first body 1013 and the third body 1015 and is connected to the needle assembly 1100. The reservoir unit 1200 may store a medical liquid D in an inner space thereof and quantitatively move the medical liquid into the needle N by moving a plunger 1230.

Figure 21:
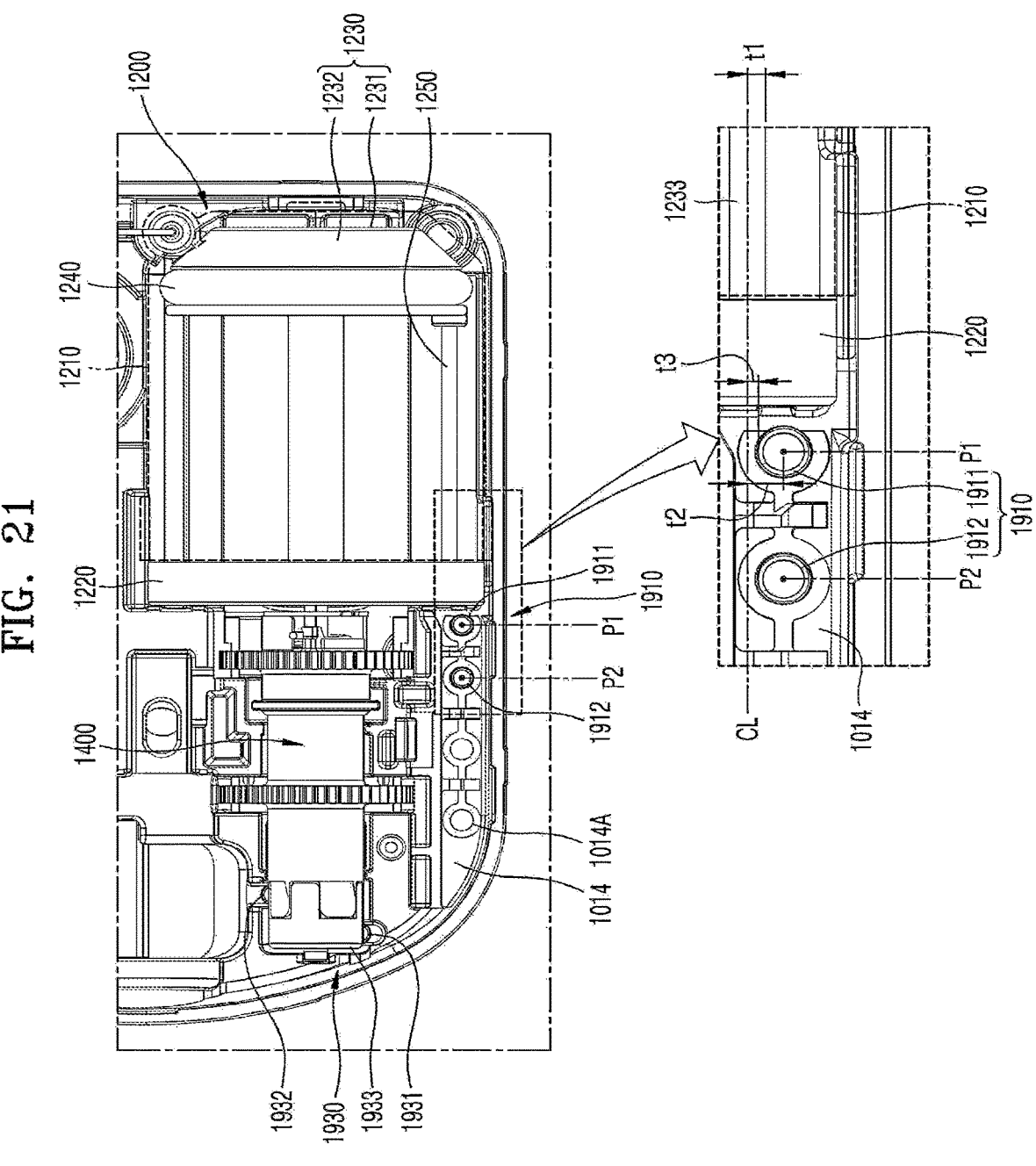
FIG. 21 is a plan view illustrating driving for sensing a flow rate of a reservoir.

Referring to FIG. 21, the reservoir unit 1200 may include the reservoir 1210, a cap cover 1220, the plunger 1230, a sealing ring 1240, and a connector member 1250.

Figure 22:
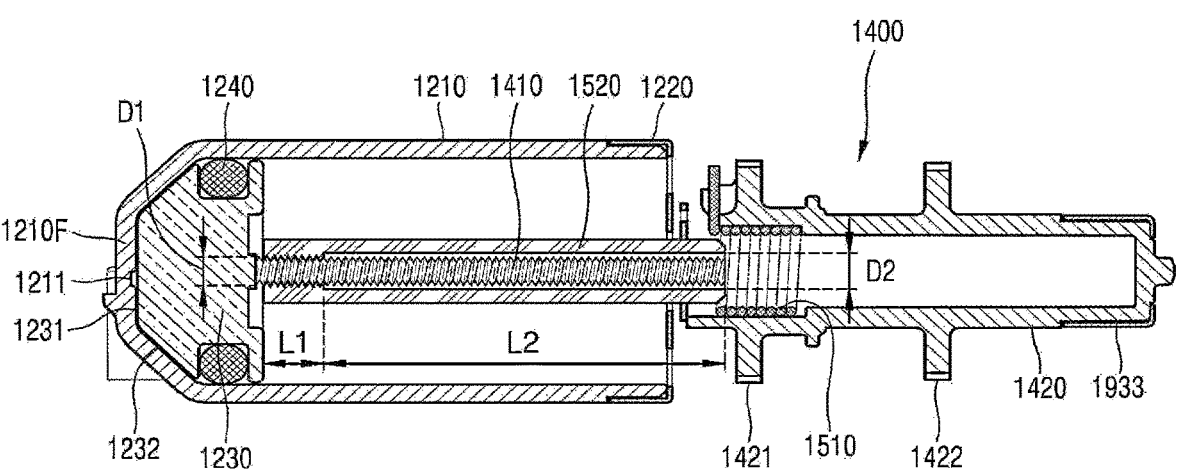
FIGS. 22 and 23 are cross-sectional views illustrating driving for injecting a medical liquid into the reservoir to store the medical liquid and discharging the medical liquid to a needle.

Referring to FIG. 22, the reservoir 1210 may extend to a predetermined length in the longitudinal direction and store a medical liquid in an inner space. In the reservoir 1210, as the plunger 1230 moves, the medical liquid may be discharged to the needle N. The cap cover 1220 may be mounted on an end portion of the reservoir 1210, and a rod 1410 and/or a connection member 1520 may move through an opening (not shown) disposed in the cap cover 1220.

The reservoir 1210 may include an inlet end and an outlet end. A medical liquid may be injected into the inlet end, the needle N may be installed at the outlet end, and the medical liquid may be discharged through the needle N.

The plunger 1230 is disposed inside the reservoir 1210 and linearly moved by the driving of the driving module 1300 and the driving unit 1400. As the plunger 1230 moves forward, the medical liquid may be discharged from the inner space into the needle N.

The plunger 1230 may include a terminating end 1231 and an inclined surface 1232. The terminating end 1231 may move toward a front side 1210F of the reservoir 1210 to move the medical liquid. The inclined surface 1232 may be in close contact with an inclined portion of the reservoir 1210.

The plunger 1230 may be connected with the connector member 1250 extending rearward. The connector member 1250 is installed in the plunger 1230, and may linearly move together with the plunger 1230 as the plunger 1230 linearly moves.

The connector member 1250 may be formed of a material having electrical conductivity and may have a shaft shape. As the connector member 1250 comes into contact with a first sensor unit 1910A while moving, a medical liquid storage amount may be measured, and driving of the medical liquid infusion apparatus 1010 may be started.

The connector member 1250 is connected to a rear end of the plunger 1230, and may move together with the plunger 1230 as the plunger 1230 moves. The connector member 1250 is illustrated in the drawings as having a shaft shape, but is not limited thereto, and may have various shapes for generating an electrical signal by coming into contact with the first sensor unit 1910A.

When a medical liquid is stored in the reservoir 1210 and the plunger 1230 moves backward, the connector member 1250 may move backward together with the plunger 1230. In addition, when the plunger 1230 moves forward so that the medical liquid is discharged from the reservoir 1210 into the needle N, the connector member 1250 may move forward together with the plunger 1230.

A sealing portion 1240 is provided on the plunger 1230 at a portion in contact with an inner sidewall of the reservoir 1210, so that a case in which a medical liquid leaks when the plunger 1230 moves may be prevented.

The driving module 1300 may generate a driving force and transmit the driving force to the driving unit 1400. The driving force transmitted by the driving unit 1400 linearly moves the plunger 1230 in the reservoir 1210 to discharge the medical liquid.

When parts in the driving unit 1400 are engaged to each other by the clutch unit 1500, the driving module 1300 rotates a driving wheel 1420 of the driving unit 1400, and the rod 1410 linearly moves by the rotation of the driving wheel 1420 to move the plunger 1230. When the plunger 1230 moves, the connector member 1250 may also linearly move together with the plunger 1230.

All types of devices having a medical liquid suction force and a medical liquid discharge force by electricity may be used as the driving module 1300. For example, all types of pumps such as a mechanical displacement type micropump and an electromagnetic motion type micropump may be used. The mechanical displacement type micropump is a pump that uses solid or fluid motion such as a gear or diaphragm to generate a pressure difference to induce fluid flow, and includes a diaphragm displacement pump, a fluid displacement pump, a rotary pump, and the like. The electromagnetic motion micropump is a pump that directly uses electrical or magnetic energy for fluid movement, and may include an electro-hydrodynamic pump (EHD), an electro-osmotic pump, a magneto-hydrodynamic pump, an electro-wetting pump, and the like.

The battery 1350 may activate each component by supplying electricity to the medical liquid infusion apparatus 1010. A pair of batteries 1350 are illustrated in the drawings, but the present disclosure is not limited thereto, and the battery 1350 may be set in various ways according to the capacity, usage range, usage time, and the like of the medical liquid infusion apparatus 1010.

The battery 1350 is disposed adjacent to the driving unit 1400, and may supply electricity to the driving unit 1400. In addition, the battery 1350 is connected to the control module 1016, and data on a rotation number or speed of the driving unit 1400, an amount of the medical liquid stored in the reservoir 1210, and an amount of the medical liquid infused into a user may be measured on the basis of an electrical signal measured by the sensor unit.

Referring to FIG. 22, the driving unit 1400 is installed between the driving module 1300 and the reservoir unit 1200, and may move the plunger 1230 disposed in the reservoir 1210 with the driving force generated by the driving module 1300. However, the driving unit 1400 may move the plunger 1230 forward only when the rod 1410 and the driving wheel 1420 are coupled or connected by the clutch unit 1500.

The rod 1410 is connected to the plunger 1230 and extends in one direction. The rod 1410 may be inserted into the opening of the cap cover 1220, and the rod 1410 may move in the longitudinal direction of the reservoir 1210 in order to move the plunger 1230. The rod 1410 may have a screw thread shape on a surface thereof. The rod 1410 is inserted into the connection member 1520, and when a medical liquid is quantitatively discharged, the rod 1410 may be connected to the driving wheel 1420 by the clutch unit 1500 and may move forward.

The driving wheel 1420 is drivingly connected to the driving module 1300, and may be rotated by the driving of the driving module 1300. The driving wheel 1420 includes a first connection terminal 1421 and a second connection terminal 1422, and may have a space therein in which the rod 1410 may move. At least one of the first connection terminal 1421 and the second connection terminal 1422 is always drivingly connected to the driving module 1300 by a connector CN, and thus the driving wheel 1420 may be rotated by the driving of the driving module 1300.

The clutch unit 1500 may drivingly connect the driving module 1300 and the driving unit 1400. The clutch unit 1500 is disposed between the rod 1410 and the driving wheel 1420, and may include a coupler 1510 and the connection member 1520.

The coupler 1510 is disposed on an outer side of the connection member 1520, is spaced apart from the connection member 1520 at a predetermined interval when deactivated (see FIGS. 22 and 23), and may connect the rod 1410 and the driving wheel 1420 when the coupler 1510 is activated. The coupler 1510 is a component capable of pressing the outer side of the connection member 1520 with an elastic force and is not limited to a specific shape. However, hereinafter, for convenience of description, a case in which the coupler has a spring shape will be mainly described.

The connection member 1520 may be disposed such that at least a portion thereof is inserted into the rod 1410. The connection member 1520 is disposed to cover an outer side of the rod 1410. The connection member 1520 may connect the driving module 1300 and the rod 1410 according to the operation of the coupler 1510.

In an embodiment, the rod 1410 and the connection member 1520 may have a screw shape and a screw thread shape, respectively. A screw thread may be formed on an outer circumferential surface of the rod 1410, and a screw thread is formed on an inner circumferential surface of the connection member 1520, and thus the rod 1410 and the connection member 1520 may be connected in a screw-coupling manner.

In an embodiment, a screw thread may be formed on one end of the inner circumferential surface of the connection member 1520 but may not be formed on the other end thereof.

Referring to FIG. 22, a screw thread is formed on the inner circumferential surface of the connection member 1520 in a first section L1, and the connection member 1520 is screw-coupled to the rod 1410 only in the first section L1. In addition, a diameter of the first section L1 may correspond to the rod 1410 and may have a size of D1.

A screw thread is not formed on the inner circumferential surface of the connection member 1520 in a second section L2. In addition, a diameter D2 of the second section L2 may be set to be greater than the diameter D1 of the first section L1. In the second section L2, the connection member 1520 is not in contact with the rod 1410.

A length of the first section L1 may be set so that the first section L1 overlaps the coupler 1510 when the connection member 1520 moves backward. When the plunger 1230 extends to a rearmost position, at least a portion of the first section L1 overlaps the coupler 1510, that is, at least a portion thereof is disposed to face the coupler 1510. The length of the first section L1 may be set in the connection member 1520 such that the coupler 1510 grips at least a portion of the first section L1 when the coupler 1510 is activated.

Since the rod 1410 is screw-coupled to the connection member 1520 only in the first section L1, when the connection member 1520 moves the rod 1410 forward while rotating, a load caused by the screw-coupling between the connection member 1520 and the rod 1410 may be reduced.

When the coupler 1510 is activated, the coupler 1510 grips the connection member 1520 and rotates together with the connection member 1520 according to the rotation of the driving wheel 1420. Since the connection member 1520 and the rod 1410 are screw-coupled only in the first section L1, the connection member 1520 may move the rod 1410 forward even when the driving wheel 1420 rotates with a small torque.

That is, since the rod 1410 and the connection member 1520 are screw-coupled only in the first section L1, the plunger 1230 may move forward by the driving the driving unit 1400 even by a relatively weak force.

Referring to FIG. 13, the trigger member 1600 according to an embodiment of the present disclosure may generate a mechanical signal that causes the medical liquid of the medical liquid infusion apparatus 1010 to be infused. The trigger member 1600 is pivotably disposed on one side of the third body 1015, and the trigger member 1600 pivots to start driving of the driving module 1300, and at the same time, the clutch unit 1500 may drivingly connect the driving unit 1400 to the driving module 1300.

The trigger member 1600 may rotate in one direction around a pivot axis. At this time, the trigger member 1600 may press the clutch unit 1500 to couple the rod to the driving wheel 1420.

In detail, when a user rotates the needle assembly 1100, a knob of the needle assembly 1100 may press an end portion of the trigger member 1600 to start the pivoting of the trigger member 1600. When the trigger member 1600 rotates, the trigger member 1600 presses an end portion of the coupler 1510, and the coupler 1510 is coupled to the connection member 1520, thereby activating the clutch unit 1500.

Referring to FIG. 13, the needle cover assembly 1700 according to an embodiment of the present disclosure may be mounted below the needle assembly 1100. The needle cover assembly 1700 may perform priming air stored in the reservoir unit 1200 before infusing a medical liquid. Gas (air) remaining in the reservoir 1210 may be discharged to the outside when the medical liquid is infused into the reservoir 1210 through a medical liquid injector NI.

The needle cover assembly 1700 may include a first cover 1710, a second cover 1720, a filter member 1730, and an adhesive layer 1740.

The first cover 1710 may be disposed on the lower portion of the medical liquid infusion apparatus 1010. The second cover 1720 may be inserted into and assembled to an opening of the first cover 1710. An insertion protrusion 1711 that is inserted into the second body 1014 to fix a needle cover assembly 1700 may be disposed on one side of the first cover 1710.

The second cover 1720 may be assembled to the first cover 1710, and the needle N and/or the cannula may be aligned to the center of the second cover 1720. The second cover 1720 may have a storage space passing through the center of the second cover 1720 in a height direction and configured to store the medical liquid D.

The first cover 1710 has a greater rigidity than the second cover 1720. The first cover 1710 is a portion exposed to the outside, and is formed of a material having a relatively larger rigidity. The second cover 1720 is assembled to the first cover 1710, and is formed of a material having a smaller rigidity than the first cover 1710 in order to be inserted into an opening of the third body 1015.

A protrusion 1721 inserted into the third body 1015 may be provided at the center of the second cover 1720. In addition, the second cover 1720 may include a fixing protrusion 1722, and the fixing protrusion 1722 may be inserted into the first cover 1710 so that the first cover 1710 is assembled to the second cover 1720.

The filter member 1730 is mounted to the second cover 1720. The filter member 1730 is disposed below the storage space of the second cover 1720, and a gas such as air passes through the filter member 1730, but a liquid such as a medical liquid does not pass through the filter member 1730. Thus, the air discharged from the needle N passes through the filter member 1730 and is discharged to the outside, but the medical liquid discharged from the needle may be stored in the storage space defined by the second cover 1720 and the filter member 1730.

The filter member 1730 may be changed in shape according to the amount of the medical liquid stored in the storage space. For example, when the storage space is filled with a medical liquid, the filter member 1730 expands downward so that a user may recognize that the medical liquid is introduced into the needle cover assembly 1700.

The adhesive layer 1740 is disposed on one surface of the needle cover assembly 1700, and may attach the needle cover assembly 1700 to the attachment portion 1012.

The alarm unit 1800 is disposed inside or outside the medical liquid infusion apparatus 1010, and a normal operation or malfunction of the medical liquid infusion apparatus 1010 may be notified to the user by the alarm unit 1800. The alarm unit 1800 may transmit an alarm to an external user by generating a warning sound or light.

The alarm unit 1800 according to an embodiment of the present disclosure is disposed below the housing 1011 and is electrically connected to the control module 1016, which is a circuit board. The control line 1016L, which is a movement path of an electrical signal for transmitting an alarm signal to the alarm unit 1800, may be formed on the control module 1016.

The control line 1016L, which is the movement path of an electrical signal, is located on the fracture portion 1162 formed to protrude outward from the control module 1016, and when the fracture portion 1162 is fractured by an external force, the movement path of an electrical signal formed on the fracture portion 1162 is also disconnected, and thus the electrical connection between the alarm unit 1800 and the control module 1016 may be disconnected.

Referring to FIGS. 19A and 19B, the control line 1016L may be disposed close to one surface (an upper surface based on FIG. 19A) of the fracture portion 1161, which faces the pass-through hole 1017H, with respect to a center portion of the fracture portion 1161 in a height direction.

Accordingly, when a user applies an external force to the fracture portion 1161 by using the tool T or the like, the control line 1016L disposed close to the surface of the fracture portion 1161 is broken first even when the fracture portion 1161, with which the tool T is brought into contact, is not completely cut, and the electrical connection between the alarm unit 1800 and the control module 1016 may be disconnected. Accordingly, when an alarm continues to be generated by the alarm unit 1800 due to an unexpected malfunction of the alarm unit 1800 in a state in which the medical liquid infusion apparatus 1010 is attached to the user, the user may fracture the fracture portion 1161 while pressing a portion, on which the fracture portion 1161 is formed, in one direction (downward direction based on FIG. 19B) by using the tool T such as a rod, and disconnect the electrical connection between the control module 1016 and the alarm unit 1800.

However, the present disclosure is not limited thereto, and the control line 1016L may be formed as a movement path of an alarm signal as well as a movement path of driving signals for the internal devices such as the plurality of sensor units, and various modified embodiments are possible, such as allowing a user to release driving of the internal device by breaking the control line 1016L located on the fracture portion 1161.

In addition, in a situation of unexpected malfunction of the alarm unit 1800 as well as in a situation of normal driving of the alarm unit 1800, when the amount of the medical liquid D becomes less than a preset amount in the process of consuming the medical liquid D, the alarm unit 1800 may be driven, and the alarm unit 1800 is driven until all capacity of the battery 1350 is consumed, and thus a situation may arise in which the driving of the alarm unit 1800 needs to be released.

In this case, the user may fracture the fracture portion 1161 by such a method and disconnect the electrical connection between the control module 1016 and the alarm unit 1800.

Referring to FIG. 20, a plurality of sensor units 1910 and 1920 may measure driving of the medical liquid infusion apparatus 1010. The plurality of sensor units 1910 and 1920 may measure an amount of medical liquid stored in the reservoir 1210, or may measure whether the driving module 1300 is driven, whether the driving unit 1400 is driven, an angle of rotation of the driving wheel 1420, a movement distance of the plunger 1230, and the like.

Each of the sensor units may have a plurality of contact terminals. Each event or data may be measured by measuring whether the contact terminal is electrically contacted.

As the contact terminal comes into contact with another component, a position of any one end portion of the contact terminal may be changed, and when the contact with another component is released, the one end portion may return to its original position by a restoring force.

Referring to FIGS. 20 and 21, an encoder unit 1930 may be disposed at one end of the driving unit 1400 and may measure rotation of the driving unit 1400. The encoder unit 1930 may measure rotation of the driving wheel 1420.

The operation principle and effect of the above-described medical liquid infusion apparatus according to an embodiment of the present disclosure will be described.

<Medical Liquid Storage Operation>

Referring to FIGS. 11 and 12, a user injects a medical liquid into the reservoir unit 1200 of the medical liquid infusion apparatus 1010 by using an external medical liquid injector (not shown).

Referring to FIG. 22, before the medical liquid is infused, the plunger 1230 is disposed at a front end of the reservoir 1210, and the rod 1410 is assembled to the connection member 1520 at a rear end of the plunger 1230. In this case, since the coupler 1510 does not grip the connection member 1520, the driving wheel 1420 is not connected to the rod 1410.

The user puts the medical liquid D to be injected into the medical liquid injector (not shown), and inserts the medical liquid injector into an inlet end of the reservoir unit 1200. At this time, air priming may be performed for air remaining inside the reservoir 1210.

In detail, in a process of assembling the reservoir unit 1200, air remains between the reservoir 1210 and the plunger 1230. When the medical liquid is infused while the air remains in the reservoir 1210, there is a risk of infusing the air to the user together, and thus an operation (priming operation) for removing the air is required.

When the medical liquid starts to flow into the reservoir 1210 from the medical liquid injector the remaining gas is pushed into the needle N as the medical liquid flows into between the plunger 1230 and an inner surface of the reservoir 1210. At this time, the gas may move along a guide groove 1211. That is, the gas remaining inside the reservoir 1210 may be discharged to the needle N along the guide of the guide groove 1211 by the flowing medical liquid D. The gas passing through the needle N moves to the needle cover assembly 1700 and passes through the filter member 1730 of the needle cover assembly 1700 to be discharged to the outside. By the guide of the guide groove 1211, the gas remaining inside the reservoir 1210 may be quickly discharged to the outside, thereby removing the gas of the reservoir 1210.

Referring to FIG. 11, by notifying the user of the fact that the medical liquid D is stored in the reservoir 1210 by a preset reference amount through the user terminal 1020 or the like, the user may be notified in advance to use the medical liquid infusion apparatus 1010.

When the plunger 1230 passes through a point P-1 according to the infusion of the medical liquid D, the connector member 1250 comes into contact with a first contact terminal 1911 at the first position P1. Thereafter, when the plunger 1230 passes through a point P-2, the connector member 1250 comes into contact with a second contact terminal 1912 at the second position P2.

In an embodiment, when the connector member 1250 electrically connects the first contact terminal 1911 and the second contact terminal 1912, a first mode is driven. The first mode is a mode in which the medical liquid infusion apparatus 1010 is woken up, and thereafter, the medical liquid infusion apparatus 1010 may be preheated so that the medical liquid infusion apparatus 1010 is immediately driven when the medical liquid infusion apparatus 1010 is attached to a user.

In addition, by notifying the user of the fact that the medical liquid D is stored in the reservoir 1210 by a preset first reference amount through the user terminal 1020 or the like, the user may be notified in advance to use the medical liquid infusion apparatus 1010.

In another embodiment, when the connector member 1250 is connected to the first contact terminal 1911, this is recognized by the control module 1016 as a first event, and when the connector member 1250 is connected to the second contact terminal 1912, this is recognized by the control module 1016 as a second event. That is, when the connector member 1250 comes into contact with each of the different contact terminals, this is recognized as a different event, and the events may be transmitted to the user.

<Attachment Operation>

Figure 23:
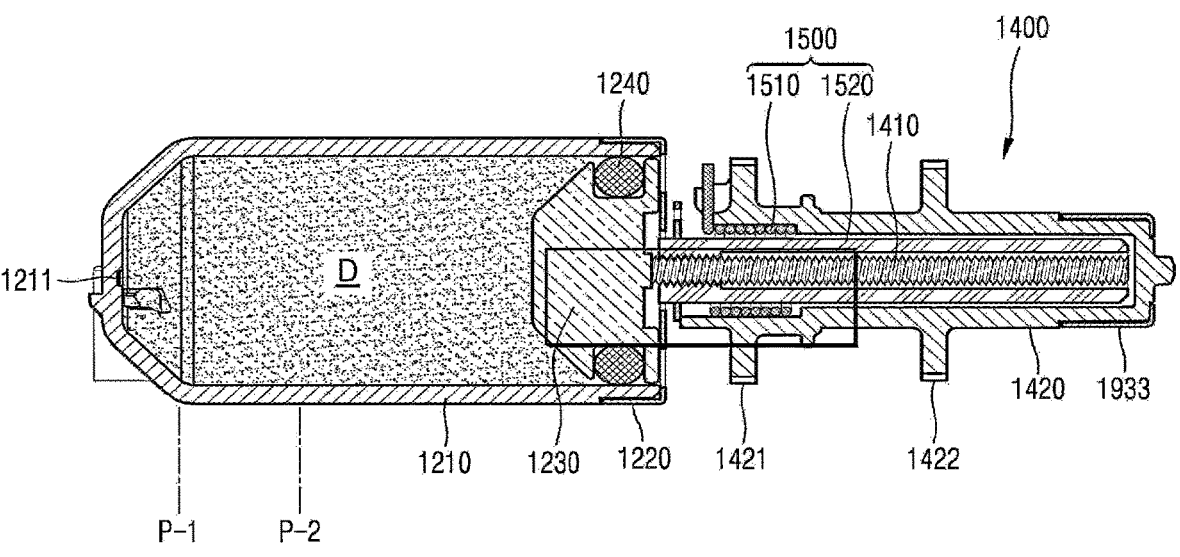

Referring to FIG. 23, when the medical liquid D stored in the reservoir 1210, the medical liquid infusion apparatus 1010 is attached to a user. Since the gas in the reservoir 1210 is removed (the priming operation is completed) through the needle cover assembly 1700 in the above-described medical liquid storage operation, the needle cover assembly 1700 is removed from the medical liquid infusion apparatus 1010.

The user attaches the medical liquid infusion apparatus 1010 thereto, rotates the needle assembly 1100, and inserts the needle N and the cannula into the skin. The needle N is inserted into the skin together with the cannula, and may induce the cannula to be inserted into the skin.

Thereafter, the needle N is withdrawn from the skin, but the state in which the needle N and the cannula are connected is maintained. When the user further rotates the needle assembly 1100, the needle N moves upward while the cannula is inserted into the skin. At least a portion of each of the cannula and the needle N is connected to each other, and a path through which the medical liquid moves is formed and maintained.

<Medical Liquid Infusion Operation-Second Mode>

The driving module 1300 and the driving unit 1400 are driven substantially simultaneously with the operation of inserting the cannula and the needle N to the user. In a second mode, the medical liquid infusion apparatus 1010 may infuse the medical liquid D into the user according to a set period and infusion amount.

When the user rotates the needle assembly 1100 to insert the needle N and the cannula into the skin, the trigger unit 1600 drives the driving module 1300.

When the user rotates the needle assembly 1100, the trigger unit 1600 may activate the coupler 1510. When the coupler 1510 grips the outer side of the connection member 1520, the driving wheel 1420, the coupler 1510, and the connection member 1520 are integrated into one body. Accordingly, when the driving wheel 1420 rotates, the connection member 1520 rotates together therewith, and the rod 1410 moves forward.

When the rod 1410 moves forward, the plunger 1230 also moves forward, thereby discharging the medical liquid into the needle N. Accordingly, the medical liquid may be infused into the user according to a set driving period and speed of the driving module 1300.

When the driving wheel 1420 rotates, the encoder unit 1930 may measure a rotation angle, a rotation speed, or the like of the driving wheel 1420.

The encoder unit 1930 may measure data related to the rotation of the driving wheel 1420 by measuring an electrical connection signal and/or an electrical release signal. The control module 1016 may calculate the rotation angle and the rotation speed of the driving wheel 1420 on the basis of the data measured by the encoder unit 1930, and calculate the movement distance of the plunger 1230 and a medical liquid discharge amount on the basis of the rotation speed and the rotation speed.

<Medical Liquid Infusion Operation-Third Mode>

When the plunger 1230 is located at a position P-2 and the connector member 1250 is located at the second position P2, the first contact terminal 1911 and the second contact terminal 1912 are electrically separated from a first sensor unit 1910.

The control module 1016 activates a third mode when the first sensor unit 1910 is electrically disconnected.

In the third mode, the control module 1016 may transmit an alarm signal indicating that the amount of the stored medical liquid corresponds to a second reference amount to the user through the user terminal 1020, the controller 1030, and/or the alarm unit 1800.

The second reference amount may be defined as an amount of medical liquid recognized by the driving module 1300 at a driving time point of the medical liquid infusion operation. The control module 1016 informs the user that the amount of the medical liquid remaining in the reservoir 1210 is the preset second reference amount, so that the user may prepare to replace the medical liquid infusion apparatus 1010.

In an embodiment, the first reference amount may be set as a medical liquid storage amount that is equal to the second reference amount. When the plunger 1230 moves forward or backward and thus the connector member 1250 is brought into contact with the second contact terminal 1912 or released from the contact with the second contact terminal 1912, the first reference amount and the second reference amount may be set to be the same since the position of the plunger 1230 in the reservoir 1210 is the same.

In another embodiment, the first reference amount may be set as a medical liquid storage amount greater than the second reference amount. The first reference amount is a reference value set for driving the first mode, and may be set to be substantially the same as the amount of the medical liquid stored in the reservoir 1210. The second reference amount is the amount of the medical liquid recognized by the driving module 1300 when the third mode starts, and may have a margin by being set to be less than the amount of the medical liquid actually remaining in the reservoir 1210.

Since the second reference amount is set to be less than the amount of the medical liquid actually stored in the reservoir 1210, the reservoir 1210 has a margin corresponding to a difference between the actual remaining amount of the medical liquid and the second reference amount. Even when the medical liquid infusion apparatus 1010 informs that there is no medical liquid, the medical liquid remaining in the reservoir 1210 may be further used, so that a sudden disconnection or accident of the medical liquid may be eliminated, thereby improving the safety of the medical liquid infusion apparatus 1010.

Since the remaining amount of the medical liquid is important in the third mode, the control module 1016 may very precisely calculate the infusion amount of the medical liquid and the remaining amount of the medical liquid in the reservoir 1210 in the third mode. When the mode is the third mode, the control module 1016 may accurately measure the rotation angle of the driving wheel 1420 and the movement distance of the plunger 1230 on the basis of the data obtained by the second sensor unit 920 and the encoder unit 1930, so that the amount of the medical liquid discharged from the reservoir 1210 and the amount of the medical liquid remaining in the reservoir 1210 may be accurately calculated. The remaining amount of the medical liquid accurately calculated in the third mode is transmitted to the user in real time so that the user may recognize a risk.

In an embodiment, the medical liquid infusion apparatus 1010 may accurately counting the amount of the medical liquid remaining in the reservoir 1210 only in the third mode. In the second mode, the amount of the medical liquid present in the reservoir 1210 is not precisely counted since the amount of the medical liquid stored in the reservoir 1210 exceeds a preset range that is, the second reference amount, but in the third mode, the amount of the medical liquid stored in the reservoir 1210 may be quantitatively counted in a set amount. Since the storage amount of the medical liquid is precisely counted only when the amount of the medical liquid stored in the medical liquid infusion apparatus 1010 reaches a level requiring an alarm, a control load of the medical liquid infusion apparatus 1010 may be reduced.

The medical liquid infusion apparatus 1010 according to an embodiment of the present disclosure may measure an infusion amount of the medical liquid stored in the reservoir 1210. The driving of the medical liquid infusion apparatus 1010 may be set by measuring the amount of the medical liquid stored in the reservoir 1210 by the first sensor unit 1910. When the plunger 1230 linearly moves inside the reservoir 1210, the connector member 1250 connected to the plunger 1230 also moves together therewith to come into contact with the first sensor unit 1910 or to release the contact with the first sensor unit 1910, so that the amount of the medical liquid stored in the reservoir 1210 may be sensed.

The medical liquid infusion apparatus 1010 according to an embodiment of the present disclosure is preheated when the reservoir is filled with the medical liquid to a certain extent, thereby increasing driving efficiency. When the amount of the medical liquid infused into the reservoir 1210 is sensed to be greater than or equal to the first reference amount by the first sensor unit 1910, the medical liquid infusion apparatus 1010 may prepare to drive some components as in the first mode and infuse the medical liquid immediately when the medical liquid infusion apparatus 1010 is attached to the user.

When the medical liquid stored in the reservoir 1210 falls below a predetermined range, this is sensed by the medical liquid infusion apparatus 1010 according to an embodiment of the present disclosure and informed to the user. When the first sensor unit 1910 senses that the amount of the medical liquid stored in the reservoir 1210 is less than or equal to the second reference amount, the medical liquid infusion apparatus 1010 may drive a second sensor unit 920 and/or the encoder unit 1930 to precisely count the amount of the medical liquid remaining in the reservoir 1210 and transmit information on the counted amount to the user.

Referring to FIGS. 12 to 18, 19A, and 19B, in a process of using the medical liquid infusion apparatus 1010 according to an embodiment of the present disclosure, it may occur that the alarm unit 1800 malfunctions due to unexpected situations.

At this time, the user may completely or partially remove the attachment portion 1012 covering one side (a lower side based on FIG. 12) of the medical liquid infusion apparatus 1010, specifically, the housing 1011.

After removing the attachment portion 1012, the user may remove the fracture cover 1018 covering the pass-through hole 1017H formed on a lower cover 1017 exposed to the outside.

Referring to FIGS. 15 to 17, 19A, and 19B, the pass-through hole 1017H formed in the lower cover 1017 may be formed at a position corresponding to the fracture portion 1161 formed to protrude outward from the control module 1016 disposed inside the housing 1011.

The control line 1016L, which is a movement path of electrical signals of the control module 1016 and the alarm unit 1800, may be located on the fracture portion 1161 formed in the control module 1016. The notch 1162 is formed in the shape of a groove while forming a boundary on the fracture portion 1161, and the plurality of notches 1162 may be provided and formed on opposite sides of the central axis of the fracture portion 1161 in the longitudinal direction.

The control line 1016L may be formed in the control module 1016 and may be located on the fracture portion 1161 on which the notch 1162 is formed. Accordingly, when the fracture portion 1161 is fractured, the control line 1016L located in the fracture portion 1161 may be broken, and the electrical connection between the alarm unit 1800 and the control module 1016 may be disconnected.

Referring to FIGS. 17, 19A, and 19B, due to the formation of the notch 1162, a predetermined section may be formed with a relatively narrow width on the fracture portion 1161, and when an external force is applied to the remaining region of the fracture portion 1161, which is relatively widely formed, stress may be concentrated in the region in which the notch 1162 is formed, and a fracture may occur.

Referring to FIGS. 18, 19A, and 19B, the first body 1013 may include the accommodation portion 1131 and the support portion 1132 formed on the control module 1016, specifically, in a region disposed to face the fracture portion 1161.

The accommodation portion 1131 is disposed such that a bottom portion is spaced a predetermined distance from the control module 1016, specifically the fracture portion 1161, and a space may be formed between the fracture portion 1161 and the bottom portion.

By forming the space between the fracture portion 1161 and the bottom portion of the accommodation portion 1131, as an external force is applied to the fracture portion 1161 in one direction (downward direction from an upper side based on FIG. 19B) by using the tool T, a space in which the fracture portion 1161 may be folded until the fracture portion 1161 is fractured may be secured, and even after the fracture portion 1161 is fractured, fragments may accommodated in the accommodation portion 1131 without moving around inside the housing 1011.

Referring to FIGS. 18, 19A, and 19B, the support portion 1132 may be formed to protrude from the bottom portion of the accommodation portion 1131 toward a predetermined region of the fracture portion 1161, specifically, the region in which the notch 1162 is formed.

As the support portion 1132 protrudes from the bottom portion of the accommodation portion 1131 and is in contact with the region in which the notch 1162 is formed, the tool T may come into contact with and support the region in which the notch 1162 is formed in a direction (an upward direction from a lower side based on FIG. 19B) opposite to a direction (a downward direction from an upper side based on FIG. 19B) in which the external force is applied to the fracture portion 1161, so that the fracture portion 1161 may be easily fractured with a relatively small force. Bu fracturing the fracture portion 1161, the electrical connection between the control module 1016 and the alarm unit 1800 may be disconnected, and the alarm unit 1800 may be forced to stop continuously generating visual or audible alarms, such as a warning sound or light, due to a malfunction.

By attaching the fracture cover 1018 to the lower cover 1017 while having a relatively larger diameter than the pass-through hole 1017H formed in the lower cover 1017, and covering the pass-through hole 1017H, a case in which the control module 1016, specifically the fracture portion 1161 disposed on an upper side (based on FIG. 13) of the lower cover 1017 in the housing 1011, is broken due to user carelessness when the alarm unit 1800 operates normally may be prevented.

A bonding means may be applied to one surface of the fracture cover 1018 facing the lower cover 1017 according to an embodiment of the present disclosure, and due to the bonding means, the fracture cover 1018 may cover the pass-through hole 1017H and a movement path to the fracture portion 1161 disposed to face the lower cover 1017 may be blocked.

However, the present disclosure is not limited thereto, and various modified embodiments are possible within the technical idea in which the fracture cover 1018 is positionally fixed to the lower cover 1017.

The medical liquid infusion apparatus 1010 according to an embodiment of the present disclosure may eliminate the inconvenience caused to a user by an alarm that is continuously provided, by allowing a preset region of the control module 1016 disposed inside the housing 1011 and electrically connected to the alarm unit 1800, specifically, the fracture portion 1161, to be fractured by an external force when necessary, such as in the event of a malfunction of the alarm unit 1800, thereby disconnecting the electrical connection between the control module 1016 and the alarm unit 1800.

Although the present disclosure has been described with reference to the embodiments illustrated in the drawings, this is merely provided as an example and it will be understood by those of ordinary skill in the art that various changes in form and details and equivalents thereof may be made. Accordingly, the true protection scope of the present disclosure should be defined only by the appended claims.

According to the present disclosure, a medical liquid infusion apparatus is provided. In addition, the embodiments of the present disclosure may be applied to commercially available medical liquid infusing devices capable of injecting a medical liquid into patients' bodies, and the like.

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. A medical liquid infusion apparatus comprising:
a first body to which a needle assembly is mounted,
a control module installed in the first body, and electrically connected to an internal device,
a fracture portion formed to protrude outward from one side of the control module, and fractured by an external force to allow an electrical connection between the control module and the internal device to be disconnected,
an alarm unit electrically connected to the control module and capable of notifying the user of normal operation or malfunction of the medical liquid infusion apparatus, and
a control line forming a movement path of an alarm signal to the alarm unit which is formed in the fracture portion.

2. The medical liquid infusion apparatus of claim 1, further comprising: a support portion formed to protrude from the first body toward the fracture portion and configured to support a preset region of the fracture portion.

3. The medical liquid infusion apparatus of claim 2, further comprising: a fracture cover disposed to face the fracture portion and configured to open and close a path through which the external force is applied to the fracture portion.

4. The medical liquid infusion apparatus of claim 1, wherein the fracture portion is formed to have a relatively narrow width in a preset region.

5. The medical liquid infusion apparatus of claim 1, further comprising:
a housing in which the first body, the control module, and the internal device are installed, and which has an opening formed on one side thereof; and
an attachment portion that covers an opening formed in the housing and is located adjacent to a user.

6. A medical liquid infusion apparatus comprising:
a first body to which a needle assembly is mounted,
a control module installed in the first body, and electrically connected to an internal device,
a fracture portion formed to protrude outward from one side of the control module, and fractured by an external force to allow an electrical connection between the control module and the internal device to be disconnected, and
a fracture cover disposed to face the fracture portion and configured to open and close a path through which the external force is applied to the fracture portion.

7. The medical liquid infusion apparatus of claim 6, further comprising: an alarm unit electrically connected to the control module and capable of notifying the user of normal operation or malfunction of the medical liquid infusion apparatus.

8. The medical liquid infusion apparatus of claim 6, wherein the fracture portion is formed to have a relatively narrow width in a preset region.

9. The medical liquid infusion apparatus of claim 6, further comprising:
a housing in which the first body, the control module, and the internal device are installed, and which has an opening formed on one side thereof; and
an attachment portion that covers an opening formed in the housing and is located adjacent to a user.

10. The medical liquid infusion apparatus of claim 6, further comprising:
a support portion formed to protrude from the first body toward the fracture portion and configured to support a preset region of the fracture portion.

11. A medical liquid infusion apparatus comprising:
a first body to which a needle assembly is mounted,
a control module installed in the first body, and electrically connected to an internal device,
a fracture portion formed to protrude outward from one side of the control module, and fractured by an external force to allow an electrical connection between the control module and the internal device to be disconnected,
an alarm unit electrically connected to the control module and capable of notifying the user of normal operation or malfunction of the medical liquid infusion apparatus,
a control line forming a movement path of an alarm signal to the alarm unit which is formed in the fracture portion, and
a support portion formed to protrude from the first body toward the fracture portion and configured to support a preset region of the fracture portion,
wherein the fracture portion is formed to have a relatively narrow width in a preset region.

12. The medical liquid infusion apparatus of claim 11, further comprising:
a housing in which the first body, the control module, and the internal device are installed, and which has an opening formed on one side thereof; and
an attachment portion that covers an opening formed in the housing and is located adjacent to a user.

13. The medical liquid infusion apparatus of claim 11, further comprising: a fracture cover disposed to face the fracture portion and configured to open and close a path through which the external force is applied to the fracture portion.

* * * * *